US007989206B2

(12) United States Patent
Viitanen et al.

(10) Patent No.: US 7,989,206 B2
(45) Date of Patent: *Aug. 2, 2011

(54) HIGH EXPRESSION ZYMOMONAS PROMOTERS

(75) Inventors: Paul V. Viitanen, West Chester, PA (US); Luan Tao, Havertown, PA (US); Yuying Zhang, New Hope, PA (US); Perry G. Caimi, Kennett Square, PA (US); Laura McCole, East Fallowfield, PA (US); Min Zhang, Lakewood, CO (US); Yat-Chen Chou, Lakewood, CO (US); Carol M. McCutchen, Wilmington, DE (US); Mary Ann Franden, Centennial, CO (US)

(73) Assignee: E.I. du Pont de Nemours and Company Alliance for Sustainable Energy LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/410,495

(22) Filed: Mar. 25, 2009

(65) Prior Publication Data

US 2009/0246876 A1 Oct. 1, 2009

Related U.S. Application Data

(60) Provisional application No. 61/039,871, filed on Mar. 27, 2008.

(51) Int. Cl.
*C07H 21/02* (2006.01)
*C07H 21/04* (2006.01)
*C12N 15/74* (2006.01)
*C12N 15/00* (2006.01)
*C12N 1/20* (2006.01)

(52) U.S. Cl. ............... 435/471; 435/476; 435/252.3; 435/320.1; 536/23.1; 536/23.4; 536/23.7; 536/24.1

(58) Field of Classification Search ............... None
See application file for complete search history.

(56) References Cited

U.S. PATENT DOCUMENTS

| 5,231,020 | A | 7/1993 | Jorgensen et al. |
| 5,514,583 | A | 5/1996 | Picataggio et al. |
| 5,712,133 | A | 1/1998 | Picataggio et al. |
| 6,566,107 | B1 | 5/2003 | Zhang |
| 7,223,575 | B2 | 5/2007 | Zhang et al. |
| 2003/0162271 | A1 | 8/2003 | Zhang et al. |
| 2007/0092957 | A1 | 4/2007 | Donalson et al. |
| 2008/0187973 | A1 | 8/2008 | Vitanen et al. |
| 2008/0286870 | A1 | 11/2008 | Vitanen et al. |

FOREIGN PATENT DOCUMENTS

WO 95/28476 A1 10/1995

OTHER PUBLICATIONS

Kobayashi et al. Nucleic Acids Research. 1990; 18:7367-7372.*
Feldmann et al., Pentose Metabolism in *Zymomonas mobilis* Wild-Type and Recombinant Strains, Appl. Microbiol. Biotechnol., 1992, vol. 38:354-361.
Zhang et al., Metabolic Engineering of a Pentose Metabolism Pathway in Ethanologenic *Zymomonas mobilis*, Science, 1995, vol. 267:240-243.
Yanase et al., Genetic Engineering of *Zymobacter palmae* for Production of Ethanol From Xylose, Appl. Environ. Microbiol., 2007, vol. 73:2592-2599.
Scott et al., Sequences of Versatile Broad-Host-Range Vectors of the RK2 Family, Plasmid, 2003, vol. 50:74-79.
Yuan et al., Chromosomal Promoter Replacement of the Isoprenoid Pathway for Enhancing Carotenoid Production in *E. coli*, Metab. Eng., 2006, vol. 8:79-90.
White et al., An Efficient System for Marketless Gene Replacement Applicable in a Wide Variety of Enterobacterial Species, Can. J. Microbiol., 2007, vol. 53:56-62.
Cahoon et al., Metabolic Redesign of Vitamin E Biosynthesis in Plants for Tocotrienol Production and Increased Antioxidant Content, Nature Biotechnology, 2003, vol. 21:1082-1087.
National Center for Biotechnology Information General Identifier No. 43692, Oct. 23, 2008, M. E. Fling et al., Nucleotide Sequence of the Transposen TN7 Gene Encoding an Aminoglycoside-Modifying Enzyme, Accession No. X03043.1.
Conway et al., Glyceraldehyde-3-Phosphate Dehydrogenase Gene From *Zymomonas mobilis*: Cloning, Sequencing, and Identification of Promoter Region, J. Bacteriol., 1987, vol. 169:5653-5662.
U.S. Appl. No. 11/862,566, filed Sep. 27, 2007, Applicant: Paul V. Vitanen.
National Center for Biotechnology Information General Identifier No. 56542470, Jul. 25, 2005, J. S. Seo, et al., *Zymomonas mobilis* Subsp. Mobilis ZM4, Complete Genome, Accession No. AE008692.

* cited by examiner

*Primary Examiner* — Robert Mondesi
*Assistant Examiner* — Oluwatosin Ogunbiyi

(57) ABSTRACT

Identified are mutants of the promoter of the *Z. mobilis* glyceraldehyde-3-phosphate dehydrogenase gene, which direct improved expression levels of operably linked heterologous nucleic acids. These are high expression promoters useful for expression of chimeric genes in *Zymomonas*, *Zymobacter*, and other related bacteria.

10 Claims, 20 Drawing Sheets

Xylose Isomerase Assay

Xyulokinase Assay

Continue to Fig. 6C

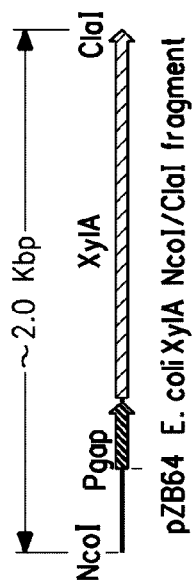
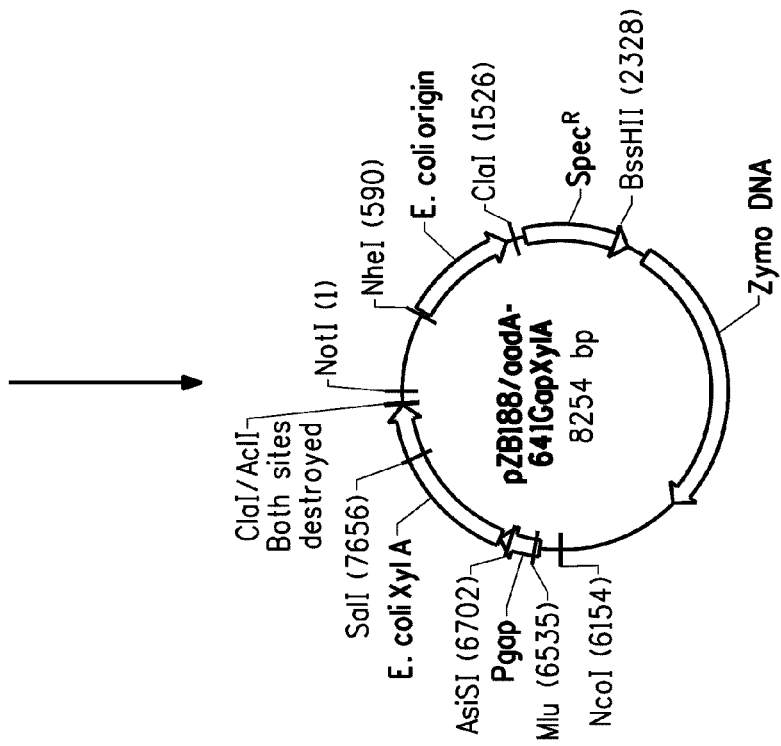
FIG. 6D
FIG. 6C

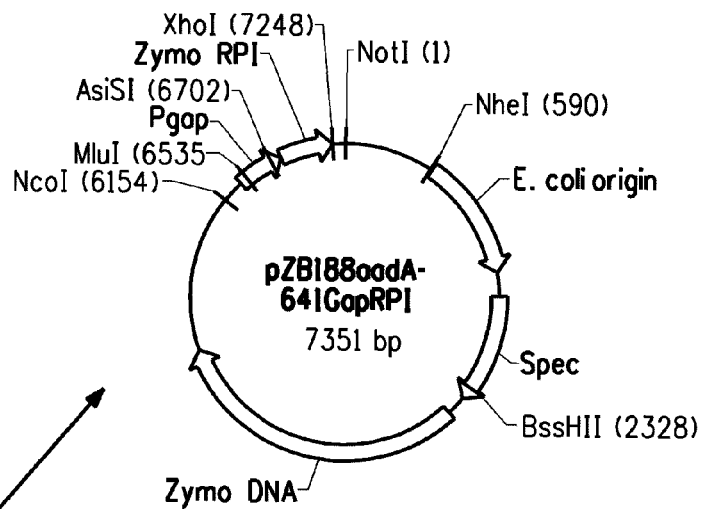
FIG. 15B
Continued from Fig. 15A

1: MW Markers
2: ZW1
3: 641gapRpi #1
4: 801gapRpi #1
5: 641gapRpi #2
6: 801gapRpi #2
7: ZW1
8: MW Markers

US 7,989,206 B2

HIGH EXPRESSION ZYMOMONAS PROMOTERS

CROSS-REFERENCE TO RELATED APPLICATION

This application claims the benefit of U.S. Provisional Application No. 61/039,871 filed on Mar. 27, 2008, which application is incorporated herein by reference.

STATEMENT OF GOVERNMENT RIGHTS

This invention was made with United States government support under Contract Nos. 04-03-CA-70224 and DE-FC36-03GO13146 awarded by the Department of Energy. The United States government has certain rights in this invention. Further, the United States Government has rights in this invention under Contract No. DE-AC36-99GO10337 between the United States Department of Energy and the National Renewable Energy Laboratory, a Division of the Midwest Research Institute.

FIELD OF INVENTION

The invention relates to the fields of microbiology and genetic engineering. More specifically, new promoters for directing expression of chimeric genes in bacteria were identified.

BACKGROUND OF INVENTION

Production of ethanol by microorganisms provides an alternative energy source to fossil fuels and is therefore an important area of current research. It is desirable that microorganisms producing ethanol, as well as other useful products, be capable of using xylose as a carbon source since xylose is the major pentose in hydrolyzed lignocellulosic materials, and therefore can provide an abundantly available, low cost carbon substrate. *Zymomonas mobilis* and other bacterial ethanologens which do not naturally utilize xylose may be genetically engineered for xylose utilization by introduction of genes encoding 1) xylose isomerase, which catalyses the conversion of xylose to xylulose; 2) xylulokinase, which phosphorylates xylulose to form xylulose 5-phosphate; 3) transketolase; and 4) transaldolase.

There has been success in engineering *Z. mobilis* strains for xylose metabolism (U.S. Pat. No. 5,514,583, U.S. Pat. No. 5,712,133, U.S. Pat. No. 6,566,107, WO 95/28476, Feldmann et al. (1992) Appl Microbiol Biotechnol 38: 354-361, Zhang et al. (1995) Science 267:240-243), as well as a *Zymobacter palmae* strain (Yanase et al. (2007) Appl. Environ. Microbiol. 73:2592-2599). However, typically the engineered strains do not grow and produce ethanol as well on xylose as on glucose. For this engineering, genes encoding the heterologous proteins for xylose metabolism have been expressed from promoters that are active in *Z. mobilis* cells, typically the promoter of the *Z. mobilis* glyceraldehyde-3-phosphate dehydrogenase gene or the promoter of the *Z. mobilis* enolase gene. Strains engineered for xylose utilization have been adapted by serial passage on xylose medium, resulting in strains with improved xylose utilization as described in U.S. Pat. No. 7,223,575 and commonly owned and co-pending U.S. Patent App. Publication No. US20080286870. However the genetic basis for the improvement had not been determined.

There remains a need for genetically engineered strains of *Zymomonas*, and other bacterial ethanolagens, having improved xylose utilization. Applicants have discovered mutant promoters having increased activity that can be used for expressing xylose utilization genes, which activity confers to engineered strains comprising these promoters improved xylose utilization. The promoters may be used for expression of other genes.

SUMMARY OF INVENTION

The present invention relates to isolated, mutant promoters for expression of genes, i.e., that is chimeric genes in *Zymomonas, Zymobacter*, and related bacteria that direct higher levels of gene expression than levels directed by the natural promoter of the *Z. mobilis* glyceraldehyde-3-phosphate dehydrogenase gene (Pgap). The mutant promoters are derivatives of the *Z. mobilis* glyceraldehyde-3-phosphate dehydrogenase gene promoter and have increased activity due to the presence of specific mutations. The promoters may be used in genetic engineering for expression of a coding region or of a regulatory RNA. Expression of a coding region for xylose isomerase directed by these promoters led to improved growth of xylose-utilizing *Zymomonas mobilis* in xylose-containing medium.

Described herein is an isolated nucleic acid molecule comprising a *Z. mobilis* glyceraldehyde-3-phosphate dehydrogenase gene promoter that has a nucleotide substitution in a position selected from the group consisting of position -190, position -89, or both position -190 and -89; wherein the position numbers are with respect to the natural ATG translation initiation codon for glyceraldehyde-3-phosphate dehydrogenase in the CP4 and ZM4 strains of *Z. mobilis*.

Also described herein are the following: a chimeric gene comprising the isolated nucleic acid molecule described above and operably linked to a heterologous nucleic acid molecule; a vector comprising the nucleic acid molecule described above and a method of genetically engineering a bacterial cell comprising introducing into the cell the nucleic acid molecule described above.

BRIEF DESCRIPTION OF THE FIGURES AND SEQUENCE DESCRIPTIONS

The various embodiments of the invention can be more fully understood from the following detailed description, the figures, and the accompanying sequence descriptions, which form a part of this application.

Figure 5:
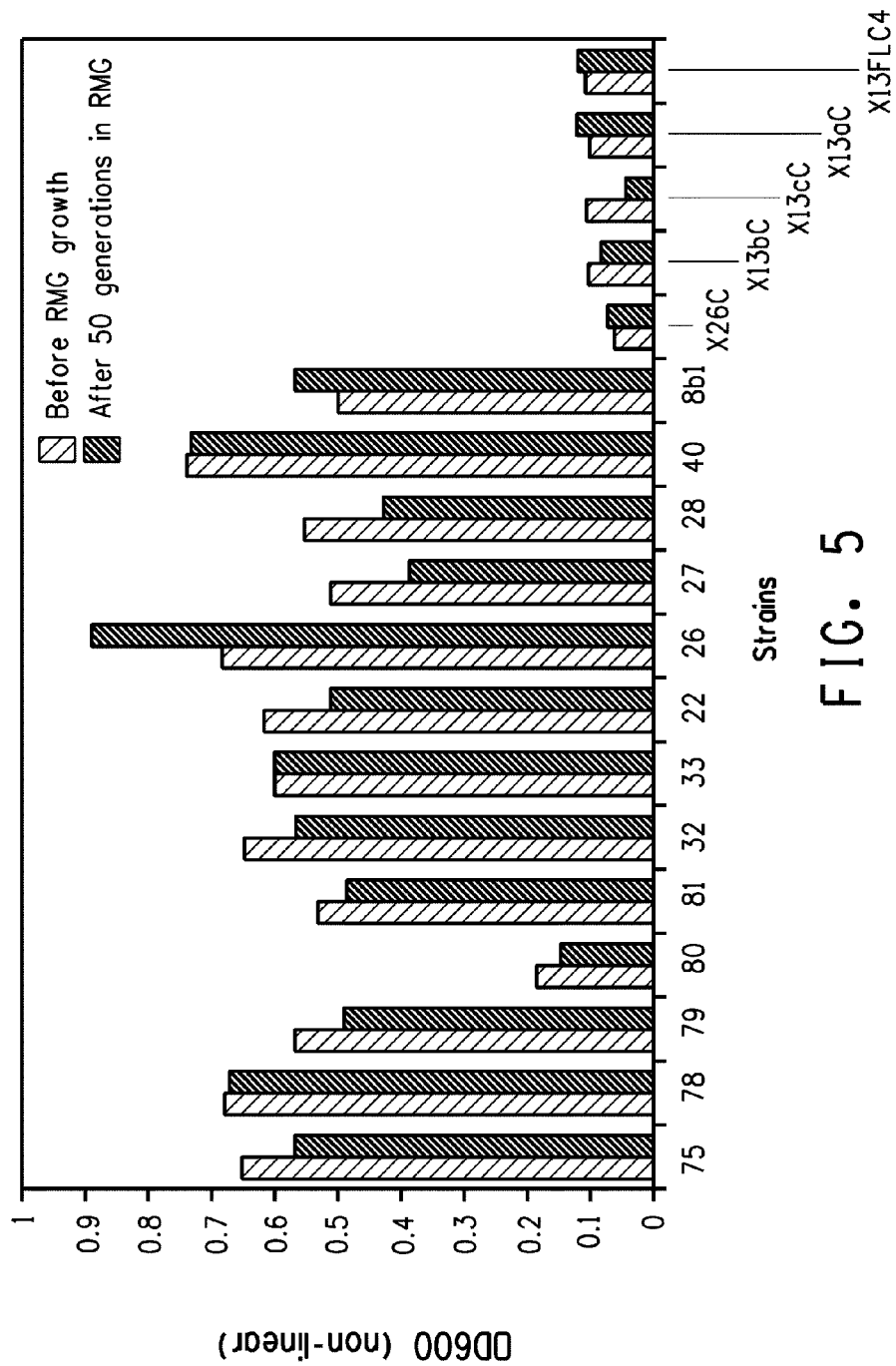

FIG. 5 shows a graph of growth of adapted xylose-utilizing strains at 70 hr on RM (rich medium) with 5% xylose (RMX5%) before and after growing 50 generations in RM with 5% glucose (RMG).

FIG. 6 shows plasmid maps of (A) pZB188; (B) pZB188/aadA; and (C) pZB188/aadA-GapXylA; as well as (D) a schematic representation of the *E. coli* xylose isomerase expression cassette PgapXylA.

FIG. 7 shows plasmid maps of (A) pMOD™-2-<MCS>; (B) pMOD-Linker; and (C) pMOD-Linker-Spec.

Figures 7C, 8:
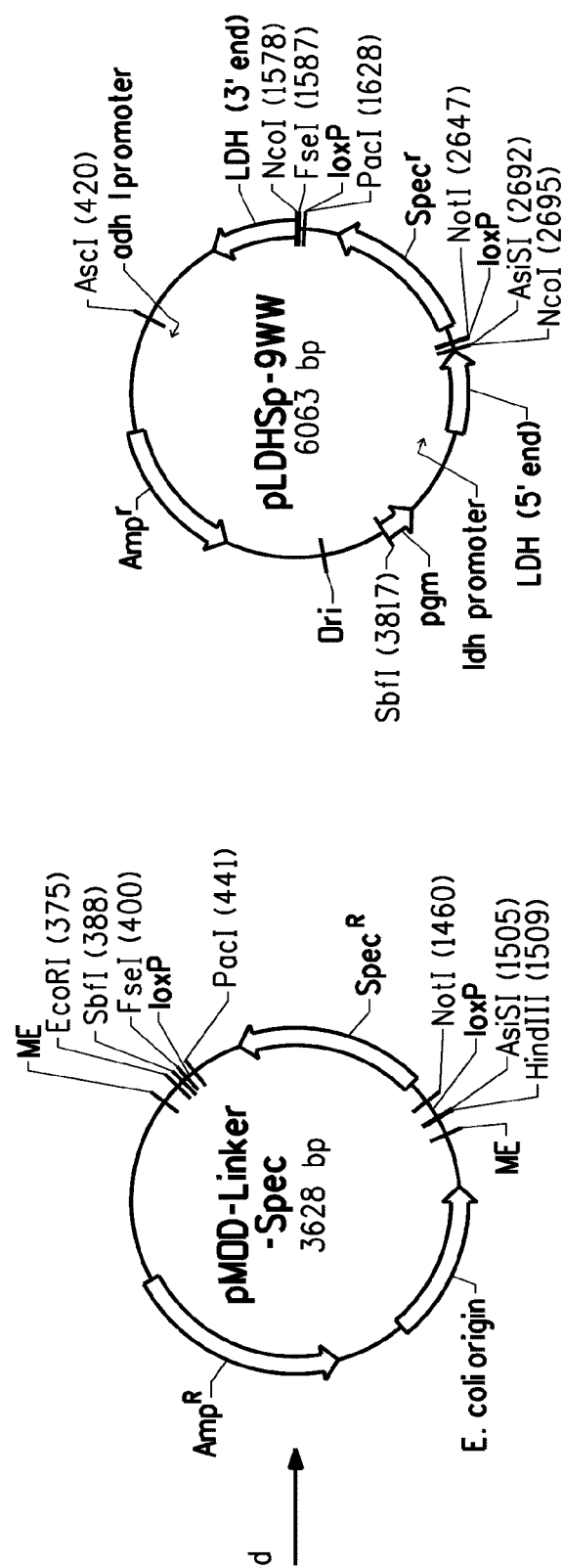

FIG. 8 shows a plasmid map of pLDHSp-9WW.

Figure 9:
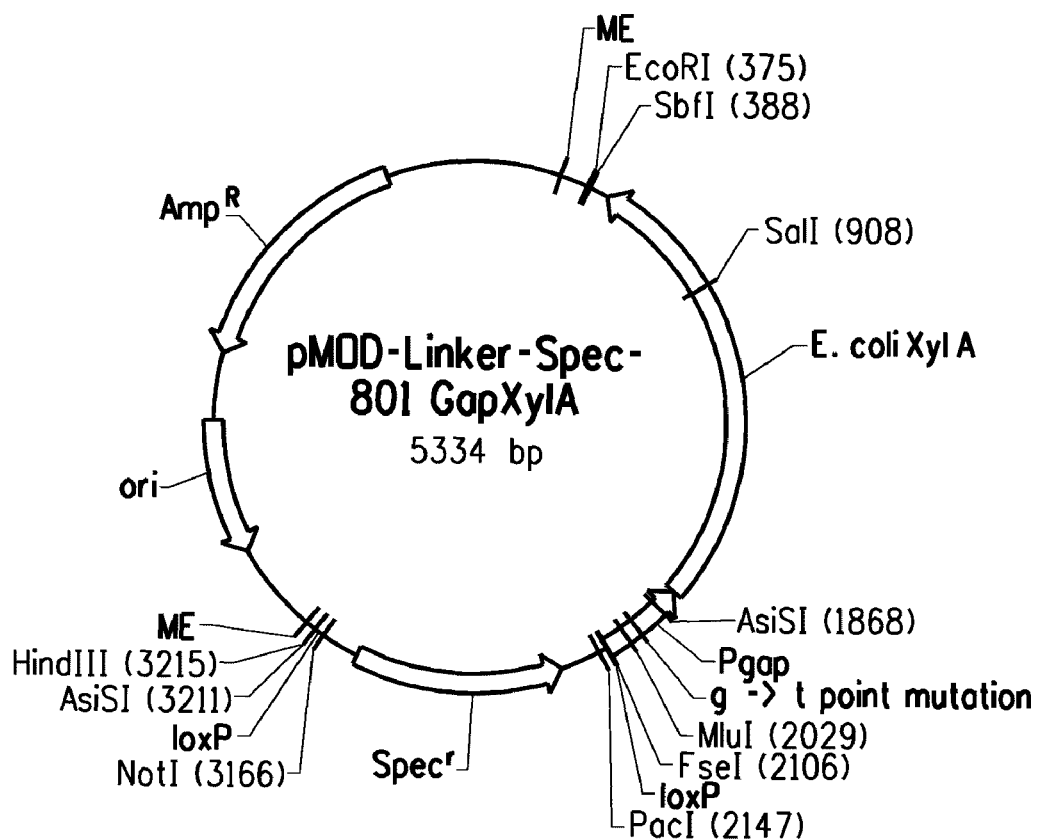

FIG. 9 shows a plasmid map of pMOD-Linker-Spec-801GapXylA.

Figure 10A:
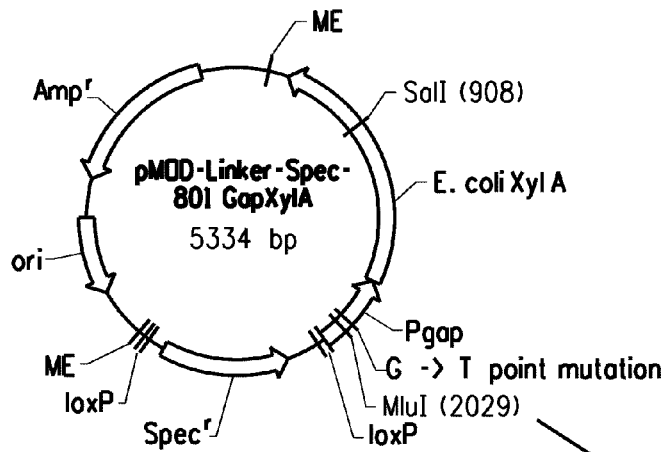
Figure 10B:
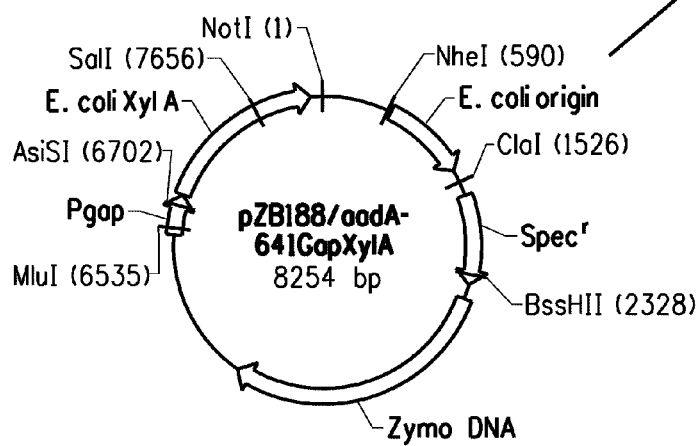

FIG. 10 shows plasmid maps of (A) pMOD-Linker-Spec-801GapXylA; (B) pZB188/aadA-GapXylA; and (C) pZB188/aadA-801GapXylA.

Figure 11:
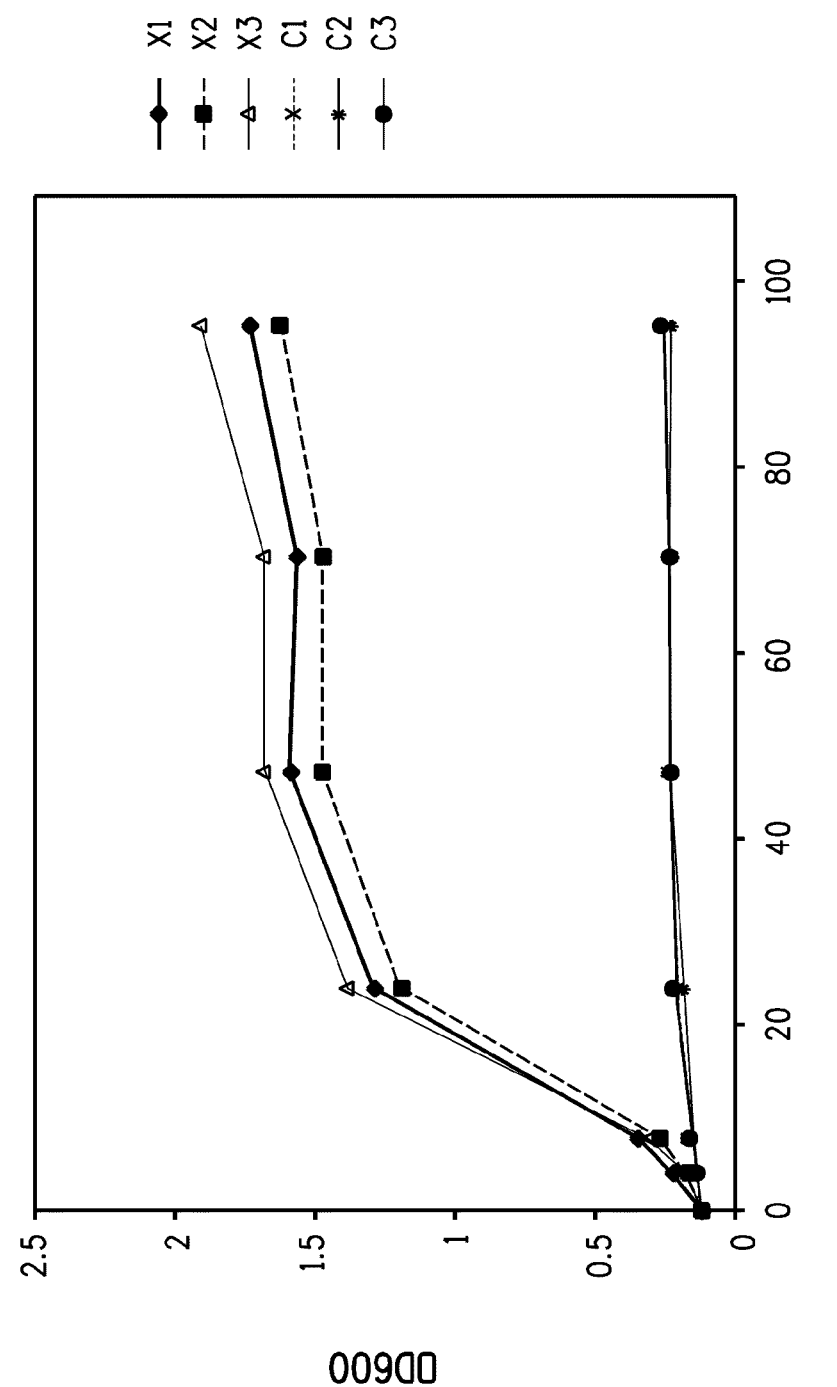

FIG. 11 shows a graph of growth curves (OD600 versus time) in xylose-containing media for the three strains that harbored the Pgap-*E. coli* xylose isomerase expression plasmid (X1, X2 and X2) and the three strains that harbored the control plasmid (C1, C2 and C3).

FIG. 12 shows graphs of growth curves (OD600 versus time) of strains ZW641, ZW658, X1 and C1 in xylose-containing media without spectinomycin plotted in (A) on a linear scale, and in (B) on a logarithmic scale.

FIG. 13 shows graphs of growth curves (OD600 versus time) of three strains with integrated 801Pgap-XylA (#8-2, #8-4, #8-5) and of three strains with integrated 641Pgap-XylA (#6-1, #6-3, #6-5) compared to strain ZW658, plotted in (A) on a linear scale, and in (B) on a logarithmic scale.

Figure 14:
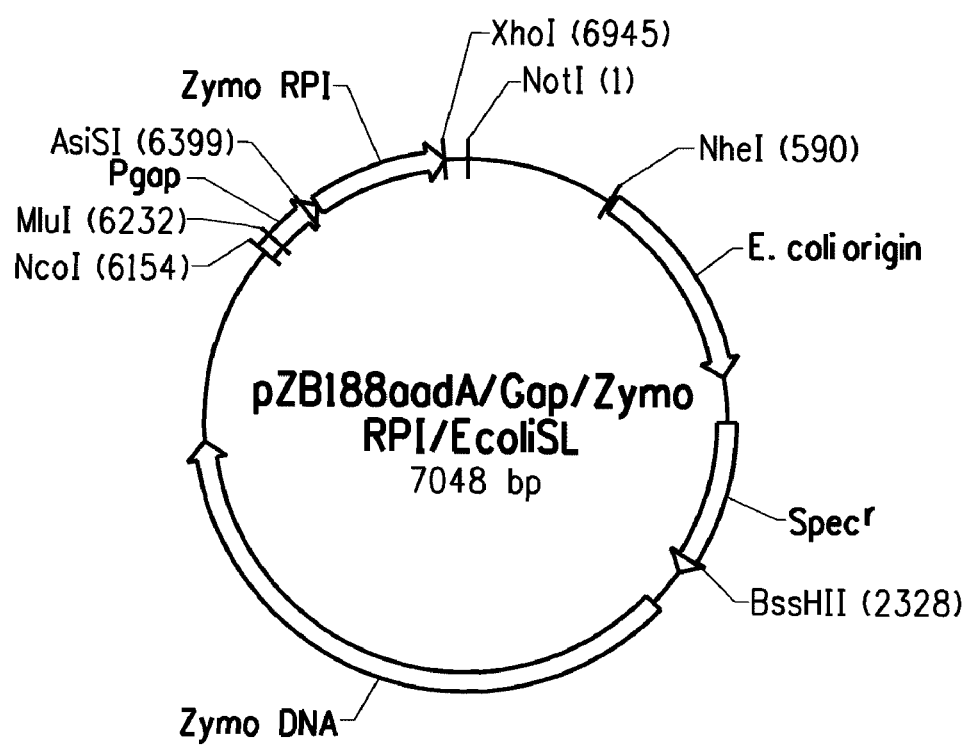

FIG. 14 shows a plasmid map of pZB188aadA/Gap/Zymo RPI/*Ecoli*SL.

FIG. 15 shows plasmid maps of (A) pZB188aadA/Gap/Zymo RPI/*Ecoli*SL; (B) pZB188aadA-641GapRPI; and (C) pZB188aadA-801GapRPI.

Figure 16:
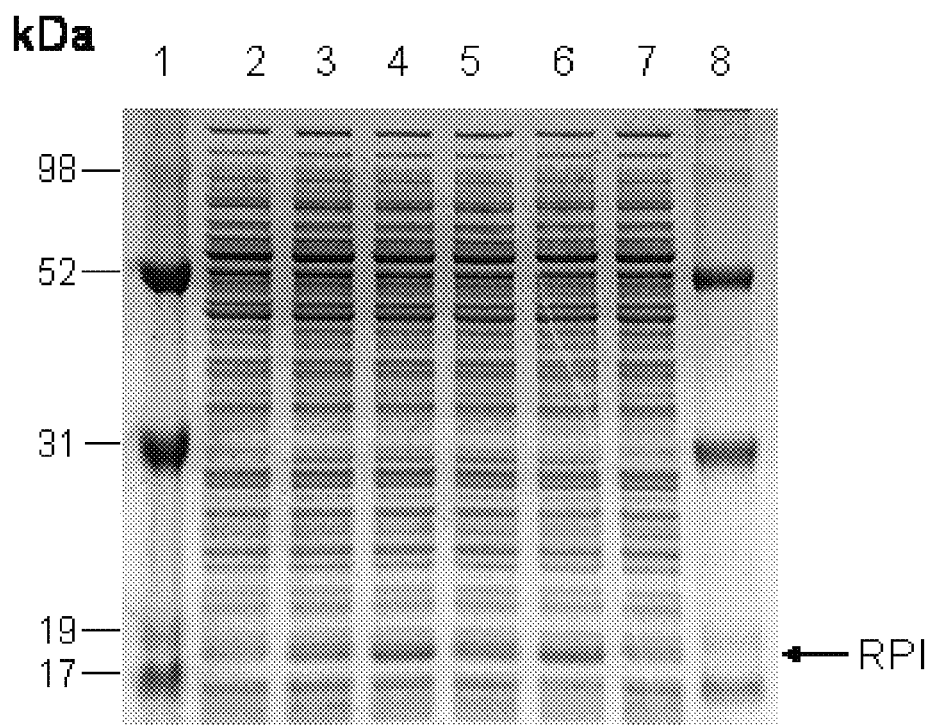

FIG. 16 shows a stained protein gel of whole cell proteins from strains with different promoters expressing RPI.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the ZmPgap from the CP4 strain of *Z. mobilis*.

SEQ ID NO:2 is the nucleotide sequence of the ZmPgap from the ZM4 strain of *Z. mobilis*.

SEQ ID NO:3 is the nucleotide sequence of the ZmPgap from pZB4, which is also in the PgapxylAB operon of strains ZW641 and 8XL4.

SEQ ID NO:4 is the nucleotide sequence of the improved Pgap from strain ZW658.

SEQ ID NO:5 is the nucleotide sequence of the improved Pgap from strain 8b.

SEQ ID NO:6 is the nucleotide sequence of an improved Pgap with both -190 (ZW658) and -89 (8b) mutations in the pZB4 variant of Pgap.

SEQ ID NO:7 is the nucleotide sequence of an improved Pgap with the -190 mutation from ZW658 in the CP4 variant of Pgap.

SEQ ID NO:8 is the nucleotide sequence of an improved Pgap with the -89 mutation from 8b in the CP4 variant of Pgap.

SEQ ID NO:9 is the nucleotide sequence of an improved Pgap with both -190 (ZW658) and -89 (8b) mutations in the CP4 variant of Pgap.

SEQ ID NO:10 is the nucleotide sequence of an improved Pgap with the -190 mutation from ZW658 in the ZM4 variant of Pgap.

SEQ ID NO:11 is the nucleotide sequence of an improved Pgap with the -89 mutation from 8b in the ZM4 variant of Pgap.

SEQ ID NO:12 is the nucleotide sequence of an improved Pgap with both -190 (ZW658) and -89 (8b) mutations in the ZM4 variant of Pgap.

SEQ ID NOs:13 and 14 are the nucleotide sequences of primers for amplification of a DNA fragment containing the glyceraldehyde-3-phosphate dehydrogenase gene promoter (Pgap) from pZB4.

SEQ ID NOs:15 and 16 are the nucleotide sequences of primers for amplification of a DNA fragment containing a tal coding region from pZB4.

SEQ ID NOs:17 and 18 are the nucleotide sequences of primers for amplification of a DNA fragment containing Pgaptal from the Pgap and tal fragments.

SEQ ID NOs:19 and 20 are the nucleotide sequences of primers for amplification of a DNA fragment containing loxP::Cm from pZB186.

SEQ ID NO:21 is the complete nucleotide sequence for the pMODPgaptaltktCm plasmid.

SEQ ID NOs:22 and 23 are the nucleotide sequences of primers for amplification of a 3 kb DNA fragment containing tal and tkt coding regions in transformants receiving pMOD-PgaptaltktCm.

SEQ ID NO:24 is the complete nucleotide sequence for the pMODPgapxy/ABCm plasmid.

SEQ ID NOs:25 and 26 are the nucleotide sequences of primers for amplification of a 1.6 kb PgapxylA DNA fragment from the T2C, T3C, T4C and T5C integrants with pMODPgapxy/ABCm.

SEQ ID NOs:27 and 28 are the nucleotide sequences of primers for amplification of a DNA fragment containing the Pgap from ZW641 and ZW658.

SEQ ID NOs:29-31 are the nucleotide sequences for primers for sequencing the Pgap from ZW641 and ZW658.

SEQ ID NOs:32 and 33 are the nucleotide sequences of primers for amplification of a DNA fragment containing a Spec$^r$-cassette.

SEQ ID NO:34 is the complete nucleotide sequence of the xylose isomerase expression cassette PgapXylA.

SEQ ID NOs:35 and 36 are the nucleotide sequences of oligonucleotides used to substitute a different multi-cloning site in pMOD2-<MCS>.

SEQ ID NOs:37 and 38 are the nucleotide sequences of primers for amplification of the PgapxylA regions from strains ZW801-4 and ZW641 for insertion into pMOD-Linker-Spec to yield plasmids pMOD-Linker-Spec-801 GapXylA and pMOD-Linker-Spec-641 GapXylA, respectively.

SEQ ID NOs:39 and 40 are the nucleotide sequences of primers for amplification of a Pgap from pZB188/aadA-641GapXylA and including the first 15 bp of the *Z. mobilis* RPI open reading frame.

SEQ ID NOs:41 and 42 are the nucleotide sequences of primers for amplification of the *Z. mobilis* RPI open reading frame SEQ ID NO:43 is the complete nucleotide sequence of the RPI expression cassette that is in plasmid pZB188aadA/Gap/Zymo RPI/*Ecoli*SL.

SEQ ID NOs:44 and 45 are the nucleotide sequences of primers for amplification of a DNA fragment containing the Pgap from 8XL4 and 8b.

SEQ ID NO:46 is the complete nucleotide sequence of a primer for sequencing the Pgap from 8XL4 and 8b.

SEQ ID NO:47 is the nucleotide sequence of a portion of ZmPgap of CP4, ZM4, and pZB4 with SEQ ID NOs:1, 2, and 3, respectively, containing position -190.

SEQ ID NO:48 is the nucleotide sequence of a portion of ZmPgap of CP4, ZM4, and pZB4 with SEQ ID NOs:1, 2, and 3, respectively, containing position -89.

DETAILED DESCRIPTION OF THE INVENTION

Described herein are new promoters that may be used for expression of chimeric genes in bacterial cells. Applicants have discovered that each of two different mutations of the *Z. mobilis* glyceraldehyde-3-phosphate dehydrogenase gene promoter separately increases the level of expression directed by the promoter. One mutation is at the -190 position, and the second mutation is at the -89 position, both with respect to the natural ATG translation initiation codon for glyceraldehyde-3-phosphate dehydrogenase in the CP4 and ZM4 strains of *Z. mobilis*. A *Z. mobilis* glyceraldehyde-3-phosphate dehydrogenase gene promoter containing either or both of these mutations may be used for expression of heterologous, operably linked DNA sequences in bacterial cells.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

"Gene" refers to a nucleic acid fragment that expresses a specific protein or functional RNA molecule, which may include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "genetic construct" refers to a nucleic acid fragment that encodes for expression of one or more specific proteins or functional RNA molecules. In the gene construct the gene may be native, chimeric, or foreign in nature. Typically a genetic construct will comprise a "coding sequence". A "coding sequence" refers to a DNA sequence that encodes a specific amino acid sequence.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts or fragments capable of suppressing the expression of identical or substantially similar foreign or endogenous genes (U.S. Pat. No. 5,231,020).

The term "messenger RNA (mRNA)" as used herein, refers to the RNA that is without introns and that can be translated into protein by the cell.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "Z. mobilis glyceraldehyde-3-phosphate dehydrogenase gene promoter" and "ZmPgap" refer to a nucleic acid molecule with promoter activity that has a nucleotide sequence that naturally occurs upstream of the glyceraldehyde-3-phosphate dehydrogenase coding region in the Z. mobilis genome. These terms refer to the promoters of strains of Z. mobilis such as the CP4 and ZM4 strains (SEQ ID NOs:1 and 2, respectively) and to variants in sequence and/or length that direct expression at a level that is not substantially different, such as the ZmPgap of pZB4 (SEQ ID NO:3).

Standard recombinant DNA and molecular cloning techniques used here are well known in the art and are described by Sambrook, J., Fritsch, E. F. and Maniatis, T. *Molecular Cloning: A Laboratory Manual*, 2$^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

Discovery of Improved Glyceraldehyde-3-Phosphate Dehydrogenase Gene Promoters

A natural promoter of the Z. mobilis glyceraldehyde-3-phosphate dehydrogenase gene (ZmPgap or Pgap) has been used for expression of chimeric genes in *Zymomonas mobilis* and *Zymobacter palmae*. When a ZmPgap has been used to express genes for xylose metabolism, the resulting xylose utilization typically has not been as effective as desired. A recombinant Z. mobilis strain engineered to express the four xylose metabolism enzymes (xylose isomerase, xylulokinase, transketolase, and transaldolase) with limited xylose utilizing ability was further adapted on xylose medium for improved xylose utilization (described in commonly owned and co-pending U.S. Pat. App. Publication. No. US20080286870).

Applicants have discovered, as described in Example 3 herein, that the improved xylose-utilizing strain called ZW658 (ATCC #PTA-7858) has increased expression of the xylose isomerase and xylulokinase enzymes that were integrated into the genome as an operon expressed from ZmPgap (PgapxylAB operon). Applicants have further discovered that there is a single new nucleotide change in the promoter of the PgapxylAB operon that is responsible for the promoter directing increased expression of operably linked coding regions. The nucleotide change is new with respect to the sequence of the Pgap of the PgapxylAB operon in strain ZW658 as compared to the sequence of the ZmPgap of the PgapxylAB operon in a precursor strain to ZW658 that did not have increased xylose isomerase and xylulokinase activities. Thus the Pgap having this single nucleotide change is an improved promoter.

Applicants have in addition discovered that a Z. mobilis strain that was separately engineered with the genes encoding the four xylose utilization enzymes and separately adapted for improved xylose utilization (strain 8b, described in U.S. Pat. No. 7,223,575) also has increased expression of the xylose isomerase and xylulokinase enzymes that were integrated into the genome as a PgapxylAB operon. Applicants have further discovered that there is a single new nucleotide change in the Pgap of the PgapxylAB operon in the 8b strain that is at a different position than the nucleotide change of the ZW658 Pgap. Based on the increased expression of the xylose isomerase and xylulokinase enzymes encoded by the PgapxylAB operon, the mutant Pgap of the PgapxylAB operon also provides an improved promoter.

The identified new nucleotide changes in the Pgap of the ZW658 and 8b strain PgapxylAB operons are at positions -190 and -89, respectively, with respect to the natural ATG translation initiation codon for glyceraldehyde-3-phosphate dehydrogenase in the CP4 and ZM4 strains of Z. mobilis. The discovered nucleotide change at position -190 is from G to T, and at position -89 is from C to T.

The sequence context of the base changes are the important factor, as the position number may change due to sequence variations.

The -190 position is in the sequence context:

(SEQ ID NO: 47)
AACGGTATACTGGAATAAATGGTCTTCGTTATGGTATTGATGTTTTT which is a portion of ZmPgap of CP4, ZM4, and pZB4 with SEQ ID NOs:1, 2, and 3, respectively, where the bold and underlined G is the base changed to T by the mutation. This position is -190 in the ZmPgap sequence of the CP4 and ZM4 strains, but position -189 in pZB4 since in the promoter sequence in pZB4 there is a deletion of T at position -21.

The -89 position is in the sequence context:

(SEQ ID NO: 48)
CGGCATCACGAACAAGGTGTTGGCCGCGATCGCCGGTAAGTCGGC which is a portion of ZmPgap of CP4, ZM4, and pZB4 with SEQ ID NOs:1, 2, and 3, respectively, where the bold and underlined C is the base changed to T by the mutation. This position is -89 in the ZmPgap sequence of the CP4 and ZM4 strains, but position -88 in pZB4 since in the promoter sequence in pZB4 there is a deletion of T at position -21. Promoters of the present invention have a nucleotide change in ZmPgap at position -190, at position -89, or at both of these positions. Preferably the changes are a G to T change at position -190 and a C to T change at position -89. The present promoters comprising these modifications are improved Pgaps.

Changes to other nucleotides at the -190 and -89 positions may provide improved activity of ZmPgap. In addition, nucleotide changes at other positions within ZmPgap may provide improved activity of promoters.

The naturally occurring sequence of ZmPgap is not a single sequence, but may have some variation in sequence that has no substantial effect on promoter function. Having no substantial effect on promoter function means that the promoter sequence directs an expression level that is substantially similar to the level of expression directed by a ZmPgap present in a natural *Zymomonas mobilis* strain. Variation in sequence may naturally occur between different isolates or strains of *Zymomonas mobilis*, such as the difference between the CP4 and ZM4 strains at position -29 with respect to the natural ATG translation initiation codon for glyceraldehyde-3-phosphate dehydrogenase (SEQ ID NOs:1 and 2, respectively), where in CP4 there is an A and in ZM4 there is a G.

In addition to naturally occurring sequence variations, nucleotide changes that do not substantially affect function may occur during routine manipulation procedures including PCR, cloning, transformation, and strain growth as is known to one skilled in the art. An example is the ZmPgap of pZB4, which has a deletion of T at position -21.

Any nucleotide changes in the ZmPgap sequence, occurring in different natural or engineered strains, that do not substantially affect promoter function, may be present in the sequence of a *Z. mobilis* glyceraldehyde-3-phosphate dehydrogenase gene promoter such as the deletion of a T after position -21 that is in the ZmPgap of pZB4 (SEQ ID NO:3). Thus the mutations at positions -190 and -89 described above that do affect promoter function, that is, that substantially improve promoter function, may be made in any of the ZmPgap sequences with substantially similar activity (natural level) and can co-occur with variations not affecting function.

Examples of improved Pgap sequences with the described mutations at positions -89 and/or -88 include the promoter sequence from strain ZW658 (SEQ ID NO:4), from strain 8b (SEQ ID NO:5), and a double mutation of the same ZmPgap variant which is from pZB4 (SEQ ID NO:6). Additional examples of improved Pgap sequences are the -190, -89, or double mutation in the ZmPgap variant from CP4 (SEQ ID NOs:7, 8, and 9, respectively) and the -190, -89, or double mutation in the ZmPgap variant from ZM4 (SEQ ID NOs:10, 11, and 12, respectively).

In addition, variations in the length of the ZmPgap occur that do not substantially affect promoter function. The present invention includes improved Pgaps having the described mutations at position -190 and/or -89 with respect to the natural ATG translation initiation codon for glyceraldehyde-3-phosphate dehydrogenase in the CP4 and ZM4 strains of *Z. mobilis* in ZmPgaps of varying length that have no substantial change in activity prior to addition of the -190 and/or -89 mutations.

Preparing an Improved Pgap

The described mutations at positions -190 and/or -89 may be introduced into a ZmPgap nucleic acid molecule by any method known to one skilled in the art. For example, an oligonucleotide having the mutation and surrounding DNA sequence may be synthesized and cloned into a larger promoter DNA fragment, substituting for a segment without the mutation. Primers containing the mutation and some adjacent promoter sequence may be synthesized and used in PCR to prepare the promoter fragment. An entire promoter DNA fragment may be synthesized as multiple oligonucleotides that are ligated together. Site-directed mutagenesis may be used to introduce the mutation(s). In addition, the mutant promoters may be prepared as PCR amplified DNA fragments using DNA from the ZW658 or 8b strain as template.

Improved Pgap in Chimeric Genes and Vectors, Introduction into Bacterial Cells

A promoter of the present invention may be operably linked to a heterologous nucleic molecule that is to be expressed in a bacterial cell, forming a chimeric nucleic acid molecule, or chimeric gene of the present invention. The designing and construction of chimeric genes are well known to one skilled in the art. A chimeric gene typically includes a promoter, a heterologous nucleic acid molecule to be expressed, and a 3' termination control region. Termination control regions may be derived from various genes, and are often taken from genes native to a target host cell. The operably linked heterologous nucleic acid molecule may be any nucleic acid molecule whose expression is desired in a bacterial cell, including, for example, a coding region for a protein or peptide, or a nucleic acid for expression of a functional RNA. Functional RNAs include, for example, antisense RNAs, ribozymes, and interfering RNAs. In addition an operon may be constructed that comprises the promoter described herein and multiple coding regions expressed from the promoter.

The promoters described herein may be used in chimeric genes for expression in bacteria belonging to *Zymomonas* or *Zymobacter*. The chimeric genes may be used for expression of any protein involved in production of a product of *Zymomonas* or *Zymobacter*. For example, one or more enzymes involved in synthesis of an amino acid such as alanine or of sorbitol or xylitol may be expressed from a chimeric gene having these promoters. The chimeric genes may be expressed in a natural *Zymomonas* or *Zymobacter* strain that does not utilize xylose, or in a xylose-utilizing strain. Also the promoters described herein may be used for expression of enzymes related to xylose metabolism or another metabolic pathway.

The chimeric genes described herein are typically constructed in or transferred to a vector for further manipulations. Vectors are well known in the art. Certain vectors are capable of replicating in a broad range of host bacteria and can be transferred by conjugation. The complete and annotated sequence of pRK404 and three related vectors: pRK437, pRK442, and pRK442(H) are available. These derivatives have proven to be valuable tools for genetic manipulation in gram-negative bacteria (Scott et al., *Plasmid* 50(1):74-79 (2003)).

Other well-known vectors may be used in different target host cells. Examples of vectors useful for different hosts are described in co-owned and co-pending US Patent Application Publication #US20070092957 A1, pp 11-13, which is hereby incorporated herein by reference. Particularly useful for expression in *Zymomonas* are vectors that can replicate in both *E. coli* and *Zymomonas*, such as pZB188 which is described in U.S. Pat. No. 5,514,583. Vectors may include plasmids for autonomous replication in a cell, and plasmids for carrying constructs to be integrated into bacterial genomes. Plasmids for DNA integration may include transposons, regions of nucleic acid sequence homologous to the target bacterial genome, or other sequences supporting integration. An additional type of vector may be a transposome produced using, for example, a system that is commercially available from EPICENTRE®. It is well known how to choose an appropriate vector for the desired target host and the desired function.

A promoter described herein may also be constructed in a vector without an operably linked nucleic acid molecule for expression, and integrated adjacent to an endogenous coding region to replace an endogenous promoter in a bacterial genome or to add a promoter, for example to a coding region within an operon. Chromosomal promoter replacements may be accomplished using methods such as described by Yuan et al (Metab. Eng. (2006) 8:79-90), and White et al. (Can. J. Microbiol. (2007) 53:56-62).

Vectors comprising a promoter described herein may be introduced into a bacterial cell by well known methods, such as using freeze-thaw transformation, calcium-mediated transformation, electroporation, or conjugation.

Expression of Heterologous Nucleic Acid Molecules Using Improved Pgap

Increased levels of chimeric gene expression may be obtained using an improved Pgap described herein. A chimeric gene constructed with an improved Pgap and a xylose isomerase coding region that was integrated into the genome was shown herein in Example 8 to allow improved growth in xylose medium of Z. mobilis cells engineered to express genes encoding proteins for xylose metabolism. Improved growth on xylose was shown herein in Examples 3 and 10 to be related to expression of higher levels of xylose isomerase activity and xylulokinase activities. Strains of xylose-utilizing Z. mobilis adapted for better growth on xylose and having an improved Pgap directing expression of xylose isomerase and xylulokinase had improved xylose utilization. Xylose isomerase and xylulokinase activities were about 4 to 5 times higher than in strains without an improved Pgap directing expression of xylose isomerase and xylulokinase.

Increased level of expression of a chimeric gene containing an improved Pgap of the present invention and located on a stable plasmid was also shown herein, in Example 9. A chimeric gene having an improved Pgap operably linked to a heterologous sequence encoding ribose 5-phosphate isomerase (RPI) produced a higher amount of RPI protein as compared to the amount produced from a chimeric gene containing a ZmPgap.

EXAMPLES

The Examples illustrate the inventions described herein.

General Methods

Standard recombinant DNA and molecular cloning techniques used here are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" means milliliter(s), "μL" means microliter(s), "μg" means microgram(s), "ng" means nanogram(s), "mM" means millimolar, "μM" means micromolar, "nm" means nanometer(s), "μmol" means micromole(s), "pmol" means picomole(s), "Cm" means chloramphenicol, "Cm$^r$" means chloramphenicol resistant, "Cm$^s$" means chloramphenicol sensitive, "Sp$^r$" means spectinomycin resistance, "Sp$^s$" means spectinomycin sensitive, "XI" is xylose isomerase, "XK" is xylulokinase, "TAL" is transaldolase, "TKT" is transketolase, "EFT" means elapsed fermentation time, "RM" means rich medium containing 10 g/L yeast extract plus 2 g/L $KH_2PO_4$, "MM" means mating medium containing 10 g/L yeast extract, 5 g/L tryptone, 2.5 g/L $(NH_4)_2SO_4$ and 0.2 g/L $KH_2PO_4$.

Preparation of Cell-Free Extracts of *Zymomonas* for Enzymatic Assays

Cells were grown in 50 ml of RM+2% glucose at 30° C. overnight to an $OD_{600}$ of 1.0-1.2. Cells were harvested by centrifugation at 4500 rpm for 10 min at 4° C. The supernatant was discarded and the cell pellet washed with 25 ml ice-cold sonication buffer (10 mM Tris, pH 7.6, 10 mM $MgCl_2$), followed by centrifugation at 4500 rpm for 10 min. The pellet was resuspended in 2.0-2.5 ml sonication buffer plus 1 mM dithiothreitol. A 500 μL aliquot was centrifuged for 1 min in an eppendorf centrifuge at 4° C. Most of supernatant was discarded, leaving about 10-20 μL behind to keep the pellet from drying out. The cells were frozen and stored at about 80° C. until assayed. Prior to assay, the cells were thawed and resuspended with 500 μL of sonication buffer plus 1 mM dithiothreitol. The mix was sonicated 2× for 45 seconds at 62% duty cycle and an output control of 2 using a Branson sonifier 450, letting samples cool about 3-5 min between sonications. Samples were centrifuged at 14,000 rpm for 60 min in a Beckman microfuge at 4° C. The supernatant was transferred to a new tube and kept at 4° C. The Pierce BCA assay was used for determining protein concentrations.

Figure 1A:
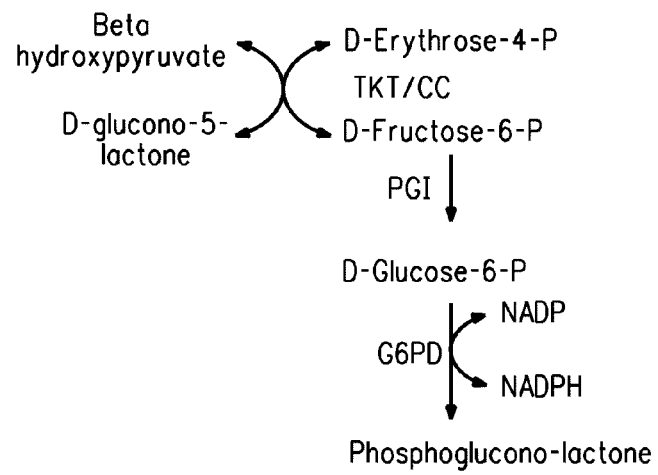
FIG. 1 shows the strategies for enzyme assays of transketolase (A), transaldolase (B), xylose isomerase (C), and xylulokinase (D).

The transketolase (TKT) assay was usually performed first since this enzyme is more labile than the others. A diagram of the TKT assay is shown in FIG. 1A.

In a microplate assay, 20 μL of cell free extract was added to each well in a reaction mix, at 30° C., that included the following final concentrations of components: 0.37 mM NADP, 50 mM TrisHCl pH 7.5, 8.4 mM Mg $Cl_2$, 0.1 mM TPP ((thiamine pyrophosphate chloride), 0.6 mM E4P (erythrose-4-phosphate), 4 mM BHP (betahydroxypyruvate), 4 U/ml PGI (phosphoglucose isomerase), and 4 U/ml G6PD (glucose-6-phosphate dehydrogenase). The $A_{340}$ was read on a plate reader for 3-5 min. TKT activity was calculated as follows:

1 unit corresponds to the formation of 1 μmol of D-fructose 6-phosphate/min at 30° C.

$U$(μmole/min)=slope($dA_{340}$/min)*volume of reaction (μL)/6220/0.55 cm(moles of NADP→NADPH is 6220 $A_{340}$ per mole per L in a 1 cm cuvette) (pathlength of 200 μL per well in microplate=0.55 cm)

Specific Activity(μmole/min–mg)=μmole/min/protein concentration(mg)

Figure 1B:
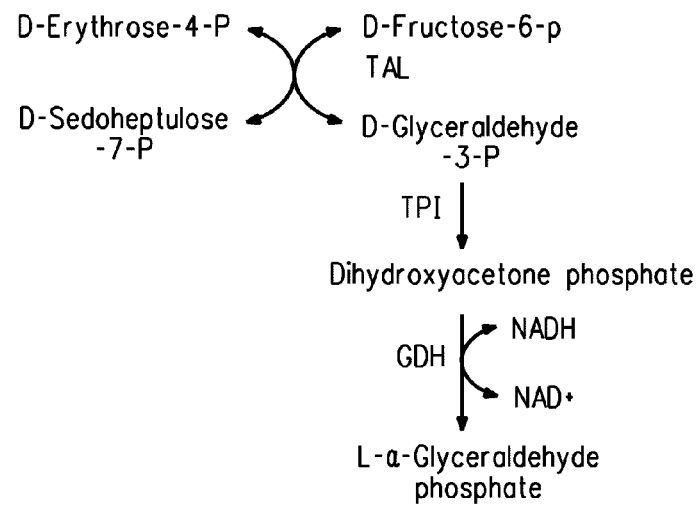

The basis of the transaldolase (TAL) assay is shown in FIG. 1B. In a microplate assay, 20 μL of cell free extract was added to each well in a reaction mix, at 30° C., that included the following final concentrations of components: 0.38 mM NADH, 87 mM triethanolamine, 17 mM EDTA, 33 mM F6P (fructose-6-phosphate), 1.2 mM E4P (erythrose-4-phosphate), 2.0 U/ml GDH (Glycerol-3-phosphate dehydrogenase), and 20 U/ml TPI (Triose phosphate isomerase). The plate was incubated for 5 min., then the $A_{340}$ was read for 3-5 min. TAL activity was calculated as follows:

1 unit corresponds to the formation of 1 μmol of D-glyceraldehyde per minute at 30° C.

$U$(μmole/min)=slope($dA_{340}$/min)*volume of reaction (μL)/6220/0.55 cm(moles of NADH→NAD is 6220 $A_{340}$ per mole per L in a 1 cm cuvette) (pathlength of 200 μL per well in microplate=0.55 cm)

Specific Activity(μmole/min–mg)=μmole/min/protein

Figure 1C:
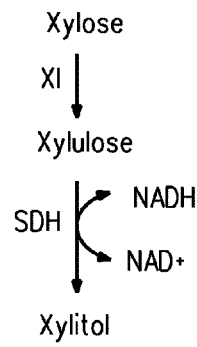

The basis of the xylose isomerase (XI) assay is shown in FIG. 1C. In a microplate assay, 20 μL of cell free extract was added to each well in a reaction mix, at 30° C., that included the following final concentrations of components: 0.256 mM NADH, 50 mM xylose, 10 mM $MgSO_4$, 10 mM triethanolamine, and 1 U/ml SDH (sorbitol dehydrogenase). The $A_{340}$ was read on a plate reader for 3-5 min. XI activity was calculated as follows:

1 unit of XI corresponds to the formation of 1 μmole of D-xylulose per minute at 30° C.

$U$(μmole/min)=slope($dA_{340}$/min)*volume of reaction (μL)/6220/0.55 cm(moles of NADHP→NAD is 6220 $A_{340}$ per mole per L in a 1 cm cuvette) (pathlength of 200 μl per well in microplate=0.55 cm)

Specific Activity(μmole/min–mg)=μmole/min/protein concentration(mg)

Figure 1D:
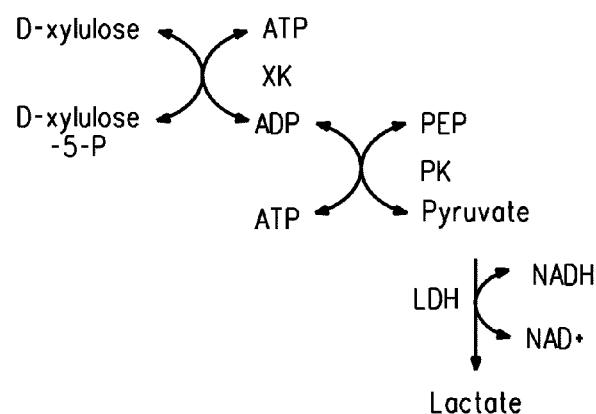

The basis of the xylulokinase (XK) assay is shown in FIG. 1D. In a microplate assay, 20 μL of cell free extract was added to each well in a reaction mix, at 30° C., that included the following final concentrations of components: 0.2 mM NADH, 50 mM Tris HCl pH 7.5, 2.0 mm $MgCl_2$-$6H_2O$, 2.0 M ATP 0.2 M PEP (phosphoenolpyruvate), 8.5 mM D-xylulose, 5 U/ml PK (pyruvate kinase), and 5 U/ml LDH (lactate dehydrognase). The $A_{340}$ was read on a plate reader for 3-5 min. XI activity was calculated as follows:
1 unit corresponds to the formation of 1 μmole of D-xylulose to D-xylulose-5-phosphate per minute at 30° C.

$U$(μmole/min)=slope($dA_{340}$/min)*volume of reaction (μL)/6220/0.55 cm(moles of NADH→NAD is 6220 $A_{340}$ per mole per L in a 1 cm cuvette) (pathlength of 200 μL per well in microplate=0.55 cm)

Specific Activity(μmole/min–mg)=μmole/min/protein concentration(mg)

HPLC Method

The analysis was done with an Agilent 1100 series HPLC and Agilent ChemStation software for LC 3D. The column was BioRad Aminex HPX-87H (HPLC Organic Analysis Column 125-0140) with BioRad Micro-Guard Cartridge Cation-H (125-0129). The operating conditions were:

| | |
|---|---|
| Flow | 0.6 ml/min |
| Solvent | 0.01 N $H_2SO_4$ |
| Stop Time | 25 min |
| Injection Volume | 5 μL |
| Auto Sampler | Temp Control @ 10° C. or 4° C. |
| Column Temp | 55° C. |
| Detector | Refractive Index (40° C.) with External Standard Calibration Curves |

Example 1

Construction of Xylose-Fermenting *Zymomonas mobilis* Strains

As described in commonly owned and co-pending U.S. App. Pub. No. US20080286870, strains of xylose-fermenting *Zymomonas mobilis* were constructed by integrating two operons, PgapxylAB and Pgaptaltkt, containing four xylose-utilizing genes encoding xylose isomerase, xylulokinase, transaldolase and transketolase, into the genome of ZW1 (ATCC #31821) via sequential transposition events, followed by adaptation on selective media containing xylose. Previously, a xylose-fermenting *Zymomonas mobilis* strain called 8b was constructed, as described in U.S. App. Pub. No. 20030162271, by integrating the two operons PgapxylAxylB and Penotaltkt, along with selectable antibiotic markers, into the genome of *Zymomonas mobilis* 5C via a combination of homologous recombination and transposon approaches followed by adaptation and NTG mutagenesis. In the preparation of new strains, transposition (Epicentre's EZ::Tn in vitro transposition system) was used, as opposed to site specific homologous recombination, because this approach offers the advantages of multiple choices of integration sites and relatively high insertion frequency. The four genes encoding the xylose utilization enzymes were arranged and cloned as two separate operons: PgapxylAB and Pgaptaltkt for the integration. An antibiotic resistance marker, a chloramphenicol resistance ($Cm^r$) gene flanked by two P1 phage Cre-recombinase recognition sequences (loxP), was attached to each operon for the selection of integrants. The integration of the two operons was accomplished in a two-step, sequential manner: Pgaptaltkt followed by PgapxylAB. Cm resistance selection was used in both integration events, since it was removed by expressing a Cre recombinase on a plasmid followed by curing of the plasmid after each integration. This process allowed the use of the same antibiotic marker for selection multiple times. More importantly, it allowed the removal of the antibiotic marker introduced for selection of the integration of the operons. This process eliminated the negative impact of antibiotic resistance gene(s) on the fermentation strain for commercial use.

Construction of pMODPgaptaltktCm for Transposition

As described in U.S. App. Pub. No. 20030162271 (Example 9 therein), a 2.2 kb DNA fragment containing the transketolase (tkt) coding region from *E. coli* was isolated from pUCtaltkt (U.S. App. Pub. No. 20030162271) by BglII/XbaI digestion and cloned in a pMOD (Epicentre Biotechnologies, Madison, Wis.) vector digested with BamHI/XbaI, resulting in pMODtkt. A PCR fragment named Pgaptal was generated by fusing the promoter region of the *Zymomonas mobilis* gap (Pgap; glyceraldehyde-3-phosphate dehydrogenase) gene to the coding region of *E. coli* transaldolase (tal) as follows. A Pgap fragment was amplified from pZB4, the construction of which is described in U.S. Pat. No. 5,514,583 (Example 3), using primers with SEQ ID NOs:13 and 14. pZB4 contains a PgapxylA/xylB operon and a Peno-tal/tkt operon. A tal coding region fragment was amplified from pZB4 using primers with SEQ ID NOs:15 and 16. A Pgaptal fragment was amplified using the Pgap and tal fragments as template using primers with SEQ ID NOs:17 and 18. This fragment was digested with XbaI and cloned into the plasmid pMODtkt, upstream of the tkt coding region. A loxP::Cm fragment was generated by PCR using Cmlox(F,sfi) and Cmlox(R,sfi) primers (SEQ ID NOs:19 and 20) and pZB186 as the template. pZB186 is a combination of a native Z. *mobilis* plasmid and pACYC184, described in U.S. Pat. No. 5,514,583 (Example 3) and Zhang et al. ((1995) Science 267:240-243). Finally, the loxP::Cm PCR fragment was inserted in the SfiI site of the plasmid containing Pgaptaltkt to form the integrative plasmid pMODPgaptaltktCm. In this plasmid, the Pgaptaltkt loxP::Cm fragment was inserted between two mosaic ends (transposase binding sites) in the pMOD vector. The complete nucleotide sequence for the pMODPgaptaltktCm plasmid is given as SEQ ID NO:21.

Transposition and Transformation of pMODPgaptaltktCm in ZW1

Plasmid pMOD is a pUC-based vector, and therefore is a non-replicative vector in *Zymomonas*. Plasmid pMODPgaptaltktCm was treated with transposase in the presence of $Mg^{2+}$ at room temperature for one hour and used to transform ZW1 cells by electroporation (using a BioRad Gene Pulser set at 200 ohms, 25 μF and 16 kV/cm). Electroporated cells were incubated in a mating medium (MM), which consists of 10 g/L yeast extract, 5 g/L tryptone, 2.5 g/L $(NH_4)_2SO_4$, 0.2 g/L $K_2HPO_4$) supplemented with 50 g/L glucose and 1 mM $MgSO_4$ for 6 hours at 30° C. The transformation mixture was plated on agar plates containing 15 g/L Bacto agar in MM supplemented with 50 g/L glucose and 120 µg/mL chloramphenicol and incubated anaerobically at 30° C. The transformants were visible after about 2 days. The transformation/transposition frequency was approx. 3×10$^1$/µg DNA.

A total of 39 Cm$^r$ transformant colonies was obtained. Twenty-one colonies were picked and further analyzed by PCR and enzymatic activity assays. PCR using primers SEQ ID NOs:22 and 23 confirmed the presence of a 3 kb DNA fragment containing tal and tkt coding regions in the transformants. Back transformation with plasmid DNA from the 21 integrant colonies generated no back transformants in *E. coli* suggesting the tal and tkt were integrated in the genome of ZW1. These integrants were tested for transaldolase and transketolase activities using protocols modified for microplates (General Methods). The Pierce BCA protein assay was used for the determination of protein concentrations. The transformants were grown up in RM medium containing 2% (w/v) glucose supplemented with 120 µg/ml chloramphenicol) in 50 ml conical centrifuge tubes at 30° C. The control strains 8b and ZW1 were grown up as well (RM plus 2% glucose was used for ZW1) for enzymatic assays. Cells were harvested when the OD$_{600}$ reached 1.0. Cells were washed once and resuspended in sonication buffer (10 mM Tris-HCl, pH 7.6 and 10 mM MgCl$_2$). Enzymatic assays were conducted as described in U.S. App. Pub. No. 20030162271. Units are given as µmole/min-mg. All samples had transaldolase and transketolase activities except for one.

Southern hybridization was performed on genomic and plasmid DNA of selected integrants digested with PstI using a tkt probe. ZW1 DNA did not hybridize with the tkt probe. A common 1.5 kb band was visible in all integrant genomic DNA samples, which is the expected DNA fragment between a PstI site in tkt and a PstI site in tal. A second visible high molecular weight (6 kb or greater) band was unique between independent lines T2, T3, T4 and T5 indicating a separate genomic integration site in each line. Interestingly, both plasmid and genomic DNA of T5 hybridized with the tkt probe indicating it was likely that Pgaptaltkt was also integrated in T5 on the native plasmid. These four strains (T2, T3, T4 and T5) were selected for further Cre treatment to remove the Cm$^r$ marker.

Cre Treatment to Remove Cm$^r$ Marker from taltkt Integrants

To remove the Cm$^r$ marker from the chromosome, T2, T3, T4 and T5 were transformed with pZB188/Spec-Cre. This plasmid is a derivative of the *Zymomonas-E. coli* shuttle vector pZB188 [Zhang et al. (1995) Science 267:240-243; U.S. Pat. No. 5,514,583] that contains an expression cassette for Cre Recombinase. pZB188/Spec-Cre is identical to the Cre Expression vector that is described In Example 10 (pZB188/Kan-Cre), except that it has a spectinomycin-resistance gene instead of a kanamycin-resistance gene. The transformants were selected on MM agar plates supplemented with 2% glucose and 200 µg/ml spectinomycin). Sp$^r$ resistant colonies were picked onto RM agar plates supplemented with 2% glucose and 200 µg/ml spectinomycin and RM agar plates supplemented with 2% glucose and 120 µg/mL Cm. One hundred percent of the colonies picked were Cm$^s$ indicating the high efficiency excision of Cm$^r$ by Cre. Sp$^r$Cm$^s$ transformants were cultured in RM plus 2% glucose at 37° C. for 2 to 5 daily transfers to cure pZB188aadACreF. At each transfer, cells were diluted and plated on RM plus 2% glucose agar plates for picking onto additional plates of the same medium with or without 200 µg/mL Sp. Sp$^s$ colonies were analyzed by PCR to confirm the loss of pZB188aadACreF. The plasmid-cured descendents of the integrants were named T2C, T3C, T4C and T5C. To examine whether these transposition integrants were stable, these 4 strains were grown in RM plus 2% glucose and then transferred to 10 ml of the same medium and grown at 37° C. in duplicate test tubes. Cells were transferred daily for ten days, or approximately 100 generations. Colonies were diluted and plated onto RMG plates for colony isolation after the 1st and 10th transfers. Twelve colonies from each transfer of each strain tested positive for the presence of Pgaptaltkt by colony PCR using 5' Pgap and 3' tkt primers (SEQ ID NOs; 13 and 23). Transaldolase and transketolase activities were also measured for isolates after the 1st and 10th transfers (as described in General Methods). All 4 integrants had similar levels of both TAL and TKT activities after 100 generations on the non-selective medium, suggesting that these integrants were genetically stable.

Construction of pMODPgapxylABCm for Transposition

The next step was to further integrate the PgapxylAB loxP::Cm operon into the ZW1::Pgaptaltkt integrants (T2C, T3C, T4C and T5C). The integrative plasmid pMODPgapxylABCm was constructed based on the plasmid pMODPgaptaltktCm (described above). The Pgaptaltkt DNA fragment was removed by SacI/SfiI digestion. An adaptor fragment containing SacI, NotI, and SfiI restriction sites was introduced by ligation. A NotI fragment of PgapxylAB, that was isolated from pZB4 (U.S. Pat. No. 5,514,583), was then cloned in the NotI site of the adaptor. Xylose isomerase (XI) is encoded by xylA and xylulokinase (XK) is encoded by xylB. The complete nucleotide sequence for the pMODPgapxylABCm plasmid is given as SEQ ID NO:24.

Transposition and Transformation of pMODPgapxylABCm in T2C, T3C, T4C and T5C

Using a similar approach to the integration of PgaptaltktCm, T2C, T3C, T4C and T5C were transformed/transposed with pMODPgapxylABCm (described above) treated with transposase. Six integrants (T3CCmX1, T3CCmX2, T3CCmX3, T4CCmX1, T5CCmX1, T5CCmX2) were obtained in 2 transformation/transposition experiments following Cm selection. All were confirmed for the presence of xylAB by PCR using two sets of primers: SEQ ID NOs:25, and 26, and SEQ ID NOs:15 and 16 except for T2CcmX1 and T2CcmX6 from which no PCR fragment was detected using the primers SEQ ID NOs:25 and 26.

Figure 2:
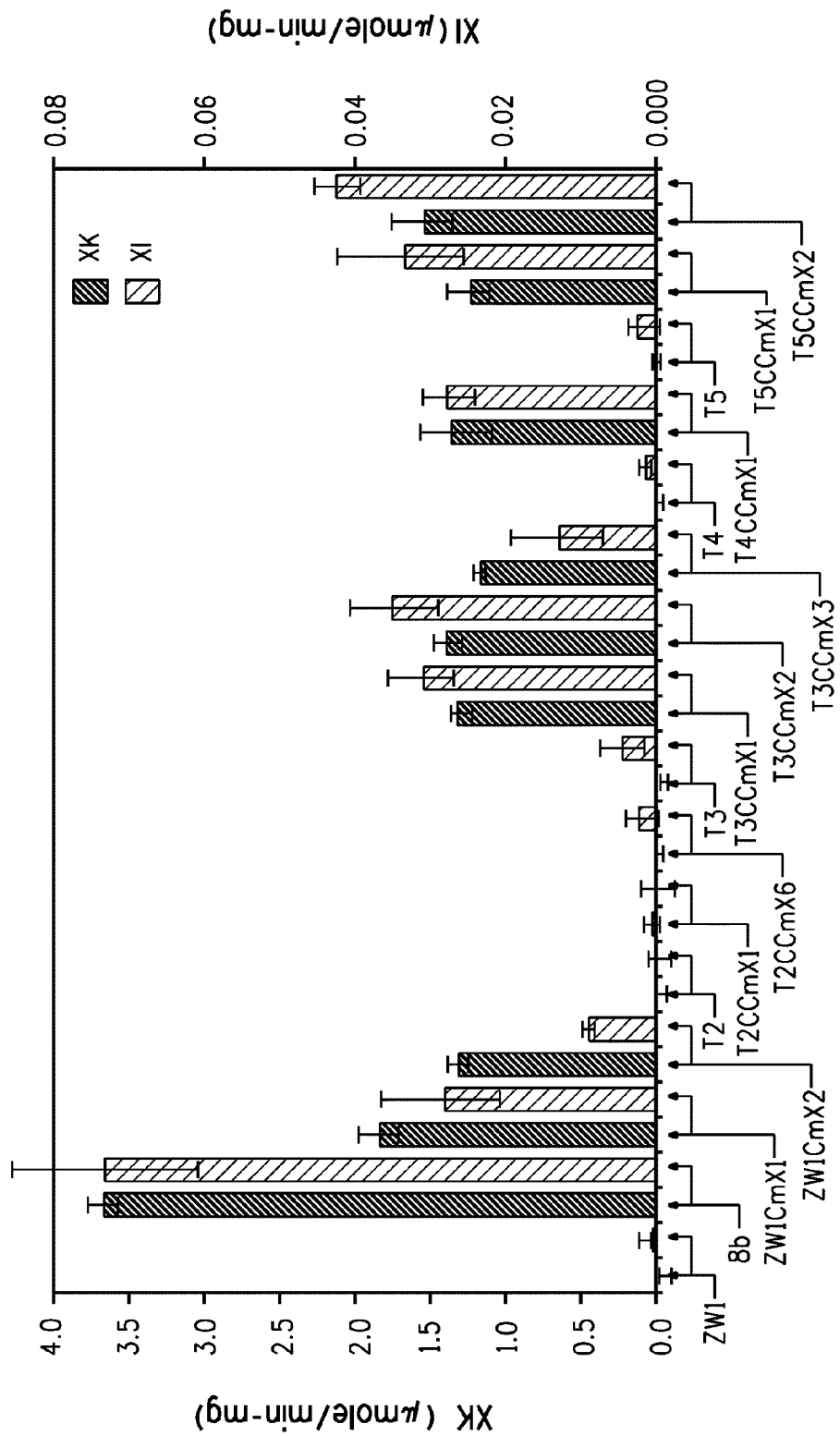
FIG. 2 shows a graph of xylose isomerase (XI) and xylulokinase (XK) activities in T2C, T3C, T4C, and T5C lines transformed with PgapxylAB.
Figure 3:
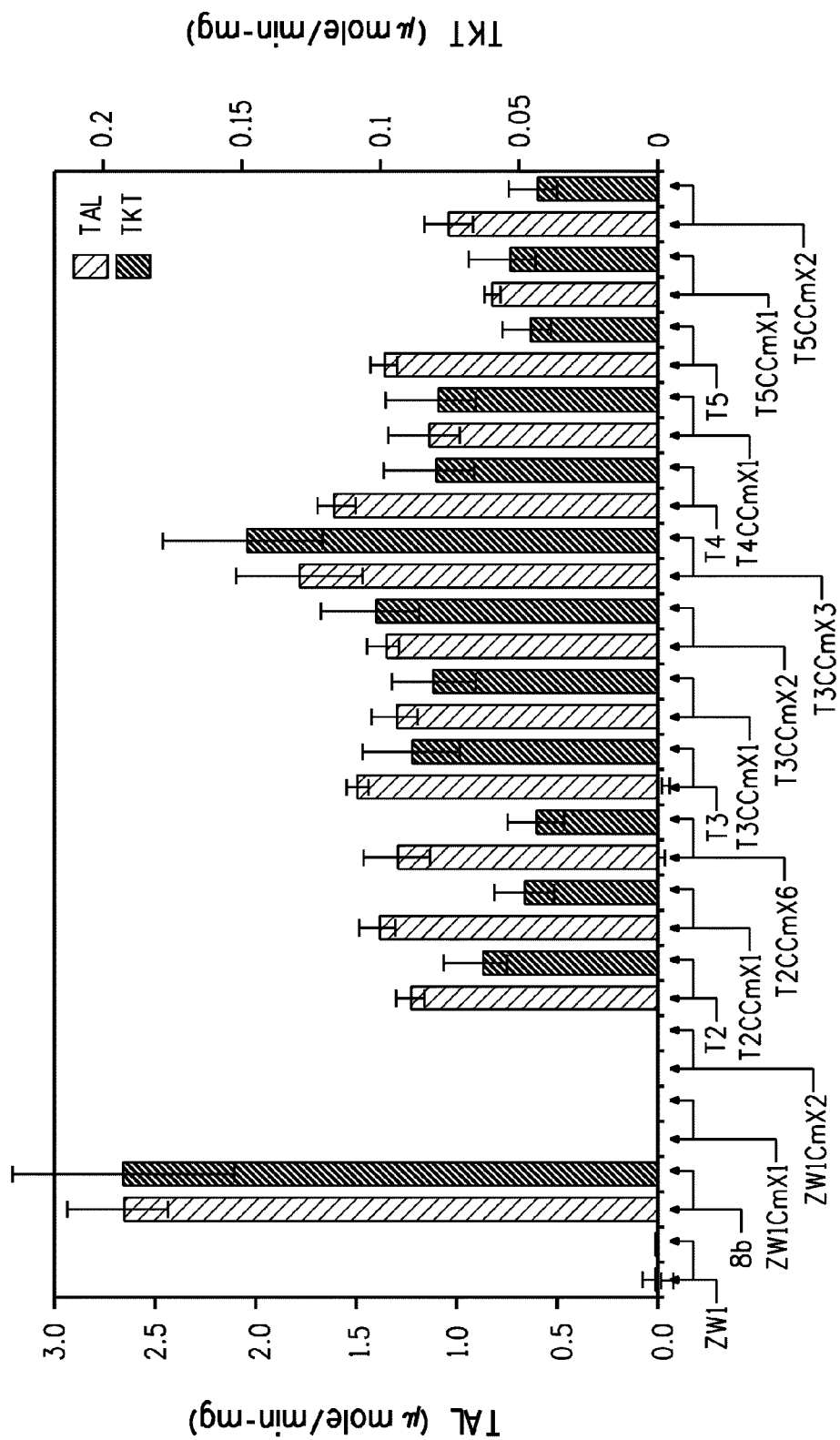
FIG. 3 shows a graph of transaldolase (TAL) and transketolase (TKT) activities in T2C, T3C, T4C, and T5C lines transformed with PgapxylAB.

The integrants, including the 2 PCR negative lines, were assayed for XI, XK, TAL and TKT activities (General Methods). The results shown in FIGS. 2 and 3 indicated that the six xylAB integrants T3CCmX1, T3CCmX2, T3CCmX3, T4CCmX1, T5CCmX1, and T5CCmX2 all had XI, XK, TAL and TKT activities. XI and XK activities were newly acquired as compared to the negative parental controls (FIG. 2). TAL and TKT activities were maintained as in the parental controls. All results indicated that the proteins were made and functional. Enzyme activity levels varied, with TI and XK activities similar to those of ZW1 integrants transformed/transposed with the same plasmid. The levels of activities of XI, XK, TAL and TKT were lower than those in strain 8b.

The integration of the xylAB operon was confirmed by Southern hybridization. Both genomic and plasmid DNA of the 6 lines were digested with SphI and hybridized to a digoxenin labeled xylB probe. A common band of about 3 kb, which is generated from an SphI site in xylB and another SphI site in the adjacent cloning sites on the pMOD vector, was present in all genomic DNA samples, and in addition, higher molecular weight hybridizing bands in the genomic DNA samples indicated that there were four sites of integration for the PgapxylAB operon in the chromosome. T3CCmX1 and T3CCmX2 appear to have the same integration site, T3CCmX3 and T4CCmX1 may have the same integration site, and T5CCmX1 and T5CCmX2 each have a separate integration site. Digestion of the same DNA with PstI followed by Southern hybridization with the tkt probe demonstrated that each integrant had the same hybridization pattern as its respective parental strain.

Adaptation of the ZW1::Pgaptaltkt PgapxylAB Cm Integrants on Xylose Media

Despite the presence of all four enzymatic activities for xylose utilization, previous observations (U.S. App. Pub. No. 20030162271) indicated that the integrants may not grow on xylose immediately. Growth on xylose may occur after prolonged incubation on xylose medium (either in test tubes or on plates), a process called adaptation.

The strains were adapted as follows. ZW1::PgaptaltktPgapxylABCm integrant strains were inoculated into test tubes containing RMX (containing 10 g/l yeast extract, 2 g/l $KH_2PO_4$, 20 g/l or 2% (w/v) xylose as well as onto MMGX or MMX plates (10 g/L yeast extract, 5 g/L of tryptone, 2.5 g/L of $(NH_4)_2SO_4$, 0.2 g/L $K_2HPO_4$, 1 mM $MgSO_4$, 1.5% (w/v) agar, 0.025% (w/v) glucose and 4% (w/v) xylose or just 4% (w/v) xylose). The low level of glucose was used to support initial growth to increase the chance of mutation during adaptation. One of at least five attempts at adaptation on xylose in both cultures and plates was successful. After 10 days of anaerobic incubation at 30° C., 17 and 19 colonies were visible on MMGX plated with T3CCmX1 and T3CCmX2 cells, respectively. The colonies were small and looked unhealthy (transparent) on the plates. Twelve colonies (four from T3CCmX1 plating: T3CCmX11, T3CCmX12, T3CCmX13 and T3CCmX110; eight from T3CCmX2 plating: T3CCmX24, T3CCmX25, T3CCmX26, T3CCmX27, T3CCmX28, T3CCmX29, T3CCmX211 and T3CCmX212) were inoculated in RMGCm120 and transferred into 3 ml RMX for further adaptation to obtain lines that were able to grow faster on xylose.

Adaptation of integrants in test tubes containing 3 ml RMX was conducted at 30° C. $OD_{600}$ was constantly monitored in a Spectronic 601 spectrophotometer. When the growth reached mid-log phase, the cultures were transferred into fresh tubes of RMX. This process was continued for 7 transfers. The growth rates and final ODs (non-linear readings) were improved over the transfers.

Figure 4:
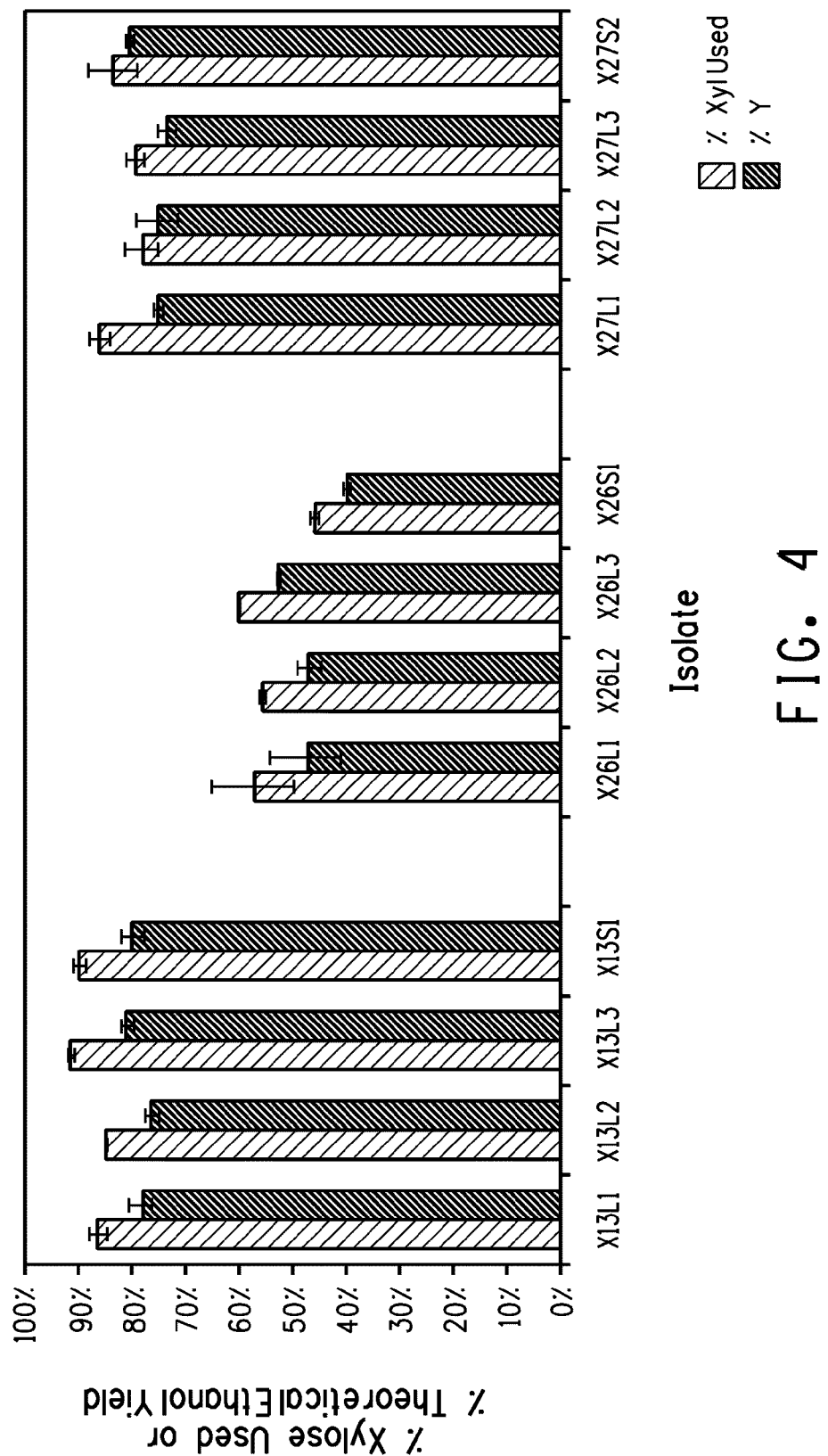
FIG. 4 shows a graph of % theoretical ethanol yield and % xylose utilization of selected adapted xylose-utilizing strain colonies.

At the $6^{th}$ transfer, the cultures were streaked out on RMX plates to isolate single colonies. Three integrants grew faster than others on RMX streaked plates: T3CCmX13, T3CCmX26 and T3CCmX27, which are referred to as X13, X26 and X27 in the tables and discussion below. To screen for the best xylose growers, four large (L1-4) and four small (S1-4) colonies each for TX13, X26 and X27 were selected and grown in RMX test tubes so that growth, sugar utilization, and ethanol production could be monitored. Colonies were grown overnight at 30° C. followed by inoculation of $OD_{600}=0.05$ into 3 ml of RMX in test tubes in duplicates. X27 grew more slowly in RMG than the other cultures and was inoculated again 6.5 hrs later. After 69 hrs (62.5 hrs for X27), samples were taken for HPLC analysis (General Methods). FIG. 4 charts the average ethanol yield (% of theoretical yield) and xylose utilization (%) for cultures at 69 hours (62.5 hr for all X27 cultures). There was no significant difference between the large and small colonies. Although the performance of X27 was better as compared to X26 on xylose, it showed slower growth on glucose. Therefore, the top performers, large colonies of X13 (X13L3) and X26 (X26L1), were chosen for further evaluation in pH-controlled fermentations. The fermentations were conducted in RMG (6% glucose), RMX (6% xylose) and RMGX (8%:4%; glucose:xylose) at 37° C. for strains X13L3 and X26L1, as well as the control strain 8b. Fermentation of glucose by X13L3 and X26L1 grown in RMG (6%) and RMGX (8%:4%) proceeded rather quickly. The fermentation of xylose in the RMGX (8%:4%) was slower for both X13L3 and X26L1 as compared to that of strain 8b. In addition, growth on RMX (6%) at 37° C. occurred after a long lag for both X13L3 and X26L1. Several isolates, X13b, X13c and X13FL, were recovered from RMX (6%) fermentations. These isolates along with the original strains X13a (an isolate of X13L3) and X26 were subjected to Cre treatment, as described previously in this Example, to remove the $Cm^r$ marker from ZW1::PgaptaltktPgapxylABCm strains. The resulting Cre treated, $Cm^r$-free integrants were named: X13aC, X13bC, X13cC, X13FLC and X26C.

Example 2

Adaptation and Selection of Strain ZW658

As described earlier, adaptation of the initial ZW1::PgaptaltktPgapxylABCm strains on RMX at 30° C. greatly improved the growth of strains in these conditions. However, the adapted strains suffered a long lag during growth and fermentation in RMX (6%) at 37° C. To further improve the integrants for xylose fermentation at preferred process conditions including higher sugar concentration and temperature, the evolutionary or adaptation process was continued in RMX (5%) at 37° C. Serial transfers were conducted and the best growers were selected. Integrants used in this process included X13aC, X13bC, X13cC, X26C and X13FLC. These 5 strains were grown in RMX at 30° C. for 6 transfers before being transferred to RMX (5%) at 37° C. for another 5 to 16 transfers. During and after all the transfers cultures were streaked on RMX plates and incubated at 37° C. to isolate single colonies. Large colonies were further streaked on RMX plates and incubated at 37° C. for 3 to 4 times to purify the colonies. Final large colonies were selected for growth testing in RMX (5%) at 37° C.

Evaluation of Strains from Adaptation in RMX (5%) Medium at 37° C.

Eighteen colonies isolated after adaptation with serial transfers were tested in RMX (5%) test tubes at 37° C. initially. Twelve strains were selected for a 2nd test tube evaluation. Strain 8b was included in all the evaluations for comparison. The 18 colonies were grown up in RMG at 37° C. overnight, centrifuged and the cells were inoculated into 4 ml of RMX (5%) at 37° C., statically in test tubes for the $1^{st}$ evaluation. Based on the growth ($OD_{600}$, non-linear) and end point HPLC results (low residual xylose and high ethanol), 12 strains were selected for the $2^{nd}$ evaluation.

One of the purposes of the $2^{nd}$ evaluation was to test the stability of improved growth on xylose and xylose utilization capability of the strains. All 12 strains were subjected to a stability study to see whether the adapted strains were stable after being exposed to a non-selective medium in which they were serially transferred in at 37° C. for 50 generations. Cultures before and after RMG (5%) transfers were inoculated in RMX (5%) test tubes and grown at 37° C. for evaluation. The non-linear ODs were monitored by direct reading of test tubes in a Spectronic 601 spectrophotometer. The ODs at the $70^{th}$ hour of growth in RMX (5%) before and after 50 generations of growth in RMG are plotted in FIG. 5. The results indicated that most strains were stable after 50 generations in RMG at 37° C. The endpoint (at stationary phase) supernatants were also analyzed by HPLC for xylose and ethanol concentrations. The low residual xylose and high ethanol concentrations in these cultures supported the fact that the strain grew and fermented xylose well.

Based on the results from the above test tube evaluation (low residual xylose, high ethanol concentration and higher OD) and a subsequent microtiter plate growth screening with high concentrations of glucose and/or xylose (up to 20%) and mixtures of glucose and xylose with acetate to select better growers in high sugars and in the presence of acetate, such as strain #26, designated as ZW658, which exhibited the best overall performance Example 3

Assay of Pentose Phosphate Pathway Enzyme Activities

The activities of the four xylose utilization enzymes encoded by integrated genes (described in Example 1) were measured as described in the General Methods for three of the strains selected for adaptation at high sugar and 37° C. (of Example 1) and were compared to activities of the same enzymes in the further adapted strain ZW658 (of Example 2). The results, expressed as μmoles product/mg protein/minute are shown in Table 1.

TABLE 1

Enzyme activities in different xylose-utilizing adapted Z. mobilis strains

| Strain | Xylose isomerase | Xylulokinase | Transaldolase | Transketolase |
|---|---|---|---|---|
| X13bC | 0.033 +/− 0.013 | 1.15 +/− 0.13 | 1.66 +/− 0.5 | 0.22 +/− 0.02 |
| ZW658 | 0.25 +/− 0.033 | 4.41 +/− 0.21 | 2.67 +/− 1.0 | 0.19 +/− 0.05 |

The activity levels for both members of the xylAB operon were increased by about 4 to 8 fold in the further adapted strain ZW658 as compared to levels in the partially adapted precursor strains. There was little or no change in the expression level of enzymes from the tal/tkt operon between ZW658 and the partially adapted precursor strains.

Example 4

Sequence Comparison of the Promoter Regions of the XylAB Operons in a Partially Adapted Strain and in ZW658

Since a clear change in the enzyme activity levels of the products of both genes under the control of the GAP promoter (Pgap) driving xylAB was a noted outcome of the adaptation that led to ZW658, the promoter region of that operon from a partially adapted strain (of Example 1; subsequently given the strain number ZW641) and from ZW658 were amplified by PCR and sequenced. A PCR fragment was prepared using a forward PCR primer (PC11; SEQ ID NO:27) from the recG coding region where the PgapxylAB operon was integrated and a reverse primer from the xylA coding region (PC12; SEQ ID NO:28). The resulting 961 bp PCR product was sequenced using primers LM121, LM122, and LM123 (SEQ ID NOs:29, 30, and 31). The promoter sequence from ZW641 is given in SEQ ID NO:3 and that from ZW658 in SEQ ID NO:4. These promoter sequences were both found to differ at one position from the published sequence of the Pgap in the Z. mobilis strain CP4 (SEQ ID NO:1): a 1 base deletion (of a T) after position -21, counting towards the 5' end starting upstream of the ATG start codon for the GAP coding region. This sequence change does not contribute to any difference in expression between the Pgap of ZW641 and Pgap of ZW658 since it is present in both strains. In addition to this common change—there was also a single base pair difference between the ZW641 and ZW658 Pgap sequences. The G at position -189 with respect to the coding region start ATG for XylA in the sequence from the ZW641 strain was replaced by a T in the sequence from ZW658. No other changes between the two sequences were noted and it seemed possible that a change in expression level due to this single base change in the GAP promoter region might be responsible for the increased enzyme activities found for both proteins encoded by genes under the control of that promoter.

Example 5

Construction of a Xylose Isomerase Expression Vector for Z. mobilis that has the Same Pgap that Drives the XylA/B Operon in Z. mobilis ZW641

Figures 6A, 6B:
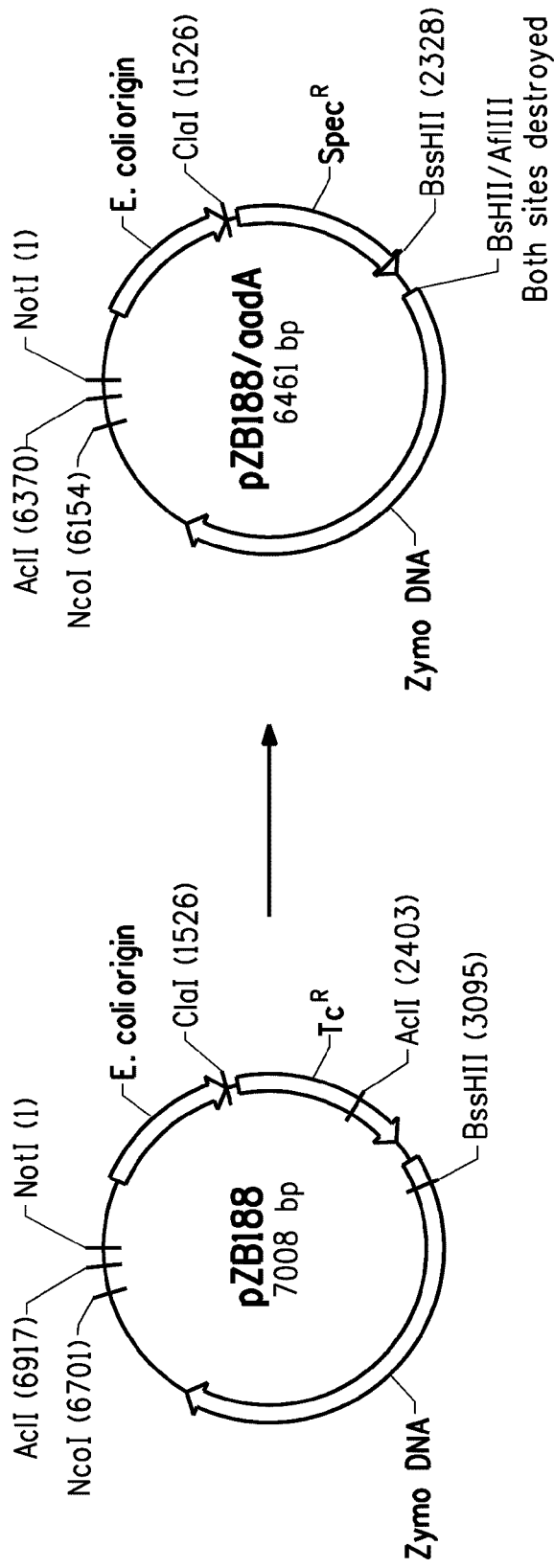

A plasmid construct that confers resistance to spectinomycin and expression of E. coli xylose isomerase in Z. mobilis (pZB188/aada-GapXylA; where Gap represents the promoter) was generated as described below using an E. coli/Z. mobilis shuttle vector (pZB188) as starting material (FIG. 6A). Steps involved in the construction of pZB188 are disclosed in U.S. Pat. No. 5,514,583. Briefly, this 7008 bp plasmid is able to replicate in E. coli and Z. mobilis because it has two different origins of replication, one for each bacterial species. pZB188 also contains a DNA fragment that confers resistance to tetracycline (i.e. a Tc$^r$-cassette). The first step in the construction of pZB188/aada-GapXylA, was to remove the Tc$^r$-cassette from pZB188 and replace it with a DNA fragment that confers resistance to spectinomycin (i.e. Spec$^r$-cassette). To excise the Tc$^r$-cassette from pZB188, the plasmid was cut with ClaI and BssHII and the resulting large vector fragment was purified by agarose gel electrophoresis as described in more detail below. The Spec$^r$-cassette was generated by PCR using plasmid pHP15578 (Cahoon et al, (2003) Nature Biotechnology 21: 1082-1087) as a template and Primers 1 (SEQ ID NO:32) and 2 (SEQ ID NO:33). Plasmid pHP15578 contains the complete nucleotide sequence for the Spec$^r$-cassette and its promoter, which is based on the published sequence of the Transposon Tn7 aadA gene (GenBank accession number X03043) that codes for 3' (9)-O-nucleotidyltransferase.

```
Primer 1
                                      (SEQ ID NO: 32)
CTACTCATTTatcgatGGAGCACAGGATGACGCCT Primer 2
                                      (SEQ ID NO: 33)
CATCTTACTacgcgtTGGCAGGTCAGCAAGTGCC
```

The underlined bases of Primer 1 (forward primer) hybridize just upstream from the promoter for the Spec$^r$-cassette (to nts 4-22 of GenBank accession number X03043), while the lower case letters correspond to a ClaI site that was added to the 5' end of the primer. The underlined bases of Primer 2 (reverse primer) hybridize about 130 bases downstream from the stop codon for the Spec$^r$-cassette (to nts 1002-1020 of GenBank accession number X03043), while the lower case letters correspond to an AflIII site that was added to the 5' end of the primer. The 1048 bp PCR-generated Spec$^r$-cassette was double-digested with ClaI and AflIII, and the resulting DNA fragment was purified using the QIAquick PCR Purification Kit (Qiagen, Cat. No. 28104) and the vendor's recommended protocol. In the next step, plasmid pZB188 (isolated from *E. coli* SSC110 (dcm$^-$, dam$^-$) in order to obtain non-methylated plasmid DNA for cutting with ClaI (which is sensitive to dam methylation) was double-digested with ClaI and BssHII to remove the Tc$^r$-cassette, and the resulting large vector fragment was purified by agarose gel electrophoresis. This DNA fragment and the cleaned up PCR product were then ligated together, and the transformation reaction mixture was introduced into *E. coli* JM110 using chemically competent cells that were obtained from Stratagene (Cat. No. 200239). Note that BssHII and AflIII generate compatible "sticky ends", but both sites are destroyed when they are ligated together. Transformants were plated on LB medium that contained spectinomycin (100 µg/ml) and grown at 37° C. A spectinomycin-resistant transformant that contained a plasmid with the correct size insert was identified by restriction digestion analysis with NotI, and the plasmid that was selected for further manipulation is referred to below as pZB188/aadA. A circle diagram of this construct is shown in FIG. 6B.

In the next step, an *E. coli* xylose isomerase expression cassette was inserted between the NcoI and AclI sites of pZB188/aadA after cutting the latter with both enzymes, and purifying the large vector fragment by agarose gel electrophoresis. The ~2 Kbp DNA fragment that served as the *E. coli* xylose isomerase expression cassette was isolated from plasmid pZB4 by cutting the latter construct with NcoI and ClaI, and purifying the relevant DNA fragment by agarose gel electrophoresis. Plasmid pZB4 is described in detail in U.S. Pat. No. 5,514,583, and a schematic representation of the *E. coli* xylose isomerase expression cassette PgapXylA (SEQ ID NO:34) is shown in the boxed diagram in FIG. 6D.

The fragment containing the *E. coli* xylose isomerase expression cassette has an NcoI site and a ClaI site at its 5' and 3' ends respectively. As described in more detail in U.S. Pat. No. 5,514,583, this fragment contains the strong, constitutive *Z. mobilis* glyceraldehyde 3-phosphate dehydrogenase (GAP) promoter (nts 316-619), which is precisely fused to the complete open reading frame of the *E. coli* xylA open reading frame (nts 620-1942) that codes for xylose isomerase. It also contains the small stem-loop region that immediately follows the xylose isomerase stop codon (nts 1965-1999). The *E. coli* xylose isomerase expression cassette was inserted between the NcoI and AclI sites of pZB188/aadA in a standard ligation reaction. Note that ClaI and AclI generate compatible "sticky ends", but both sites are destroyed when they are ligated together. The ligation reaction mixture was then electroporated into *E. coli* SSC110 (dcm$^-$, dam$^-$) to obtain non-methylated plasmid DNA for subsequent transformation of *Z. mobilis*, and the transformed cells were plated on LB medium that contained 100 µg/ml of spectinomycin; growth was at 37° C. Spectinomycin-resistant transformants that had a plasmid with a correct size insert were identified by restriction digestion analysis with NotI, NcoI and AclI. The plasmid that was selected for further manipulation and overexpression of *E. coli* xylose isomerase in the *Z. mobilis* ZW641 strain is referred to below as "pZB188/aadA-641GapXylA"; a circle diagram of this plasmid construct is shown in FIG. 6C.

It is important to note that the nucleotide sequence of SEQ ID NO:34 is not identical to the nucleotide sequence that is described in SEQ ID NO:34 in co-owned and co-pending U.S. App. Pub. Nos. US20080286870 and US20080187973, even though it corresponds to the same *E. coli* xylose isomerase expression cassette (PgapXylA). The DNA sequence disclosed in SEQ ID NO: 34 in the present work has a 1-bp deletion in the Pgap that corresponds to nt 599 of SEQ ID NO:34 in U.S. App. Pub. Nos. US20080286870 and US20080187973. The nucleotide sequence that was reported in the earlier patent applications was based on the published DNA sequence of the Pgap for the *Z. mobilis* strain CP4 (Conway et al. J. Bacteriol. 169 (12):5653-5662 (1987)) and the promoter was not resequenced at that time. Recently, however, we have discovered that the Pgap in pZB4 is also missing the same nucleotide, and the *E. coli* xylose isomerase expression cassette (PgapXylA) that was used for all three patent applications was derived from this plasmid as noted above.

Example 6

Generation of an *E. coli* Xylose Isomerase Expression Vector that has the Same Pgap that Drives the XylA/B Operon in *Z. mobilis* ZW658 and ZW801-4

Plasmid pZB188/aadA-801GapXylA is identical to pZB188-aadA-641GapXylA (FIG. 6C) but has a single bp substitution in the Pgap that corresponds to the G->T mutation that is present at position -189 in the Pgap that drives expression of the *E. coli* XylA/B operon in ZW658. The same point mutation is also present in strains ZW800 and ZW801-4, which were sequentially derived from ZW658 as described below. The construction and characterization of ZW800 and ZW801-4 are described in great detail in commonly owned and co-pending U.S. App. Pub. No. US20080286870. ZW800 is a derivative of ZW658 which has a double-cross-over insertion of a spectinomycin resistance cassette in the sequence encoding the glucose-fructose oxidoreductase (GFOR) enzyme that inactivates this activity. ZW801-4 is a derivative of ZW800 in which the spectinomycin resistance cassette was deleted by site-specific recombination leaving an in-frame stop codon that prematurely truncates the protein. None of these manipulations altered the nucleotide sequence of the mutant Pgap promoter that drives the XylA/B operon in ZW658. Thus, the "801GAP promoter" refers to the promoter sequence that is present in the following strains: ZW658, ZW800, and ZW801-4.

Figures 7A, 7B:
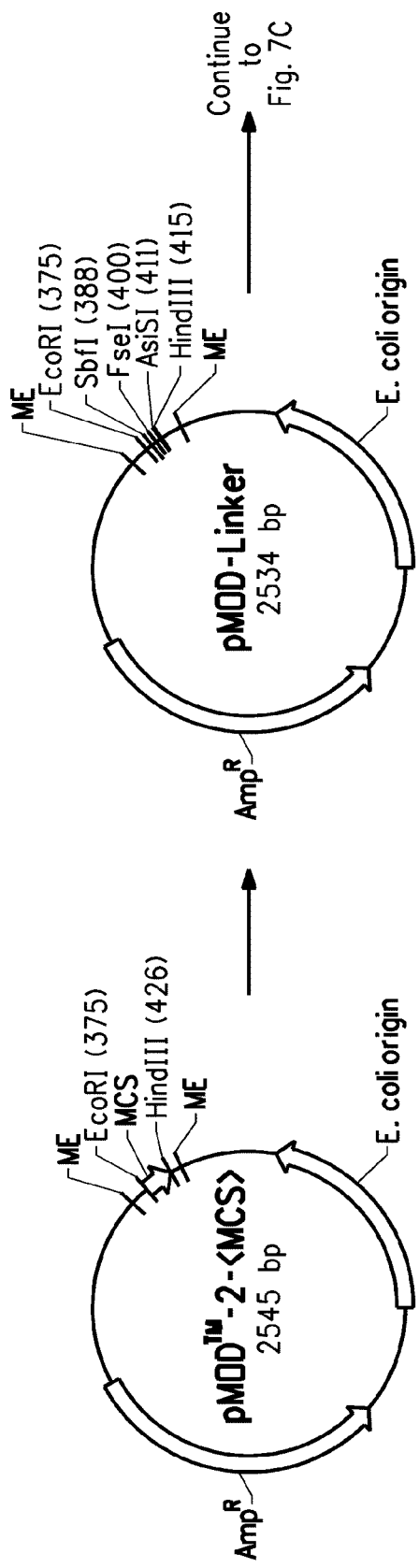

The steps and plasmid intermediates that were used to generate pZB188/aadA-801GapXylA are described below in chronological order starting with the plasmid pMOD-Linker. Construction of pMOD-Linker The precursor for plasmid pMOD-Linker was the pMOD™-2<MCS> Transposon Construction Vector (Cat. No. MOD0602) that is commercially available from EPICENTRE®. As shown in FIG. 7A, pMOD™-2<MCS> has an ampicillin resistance gene (ampR), an *E. coli* origin of replication (ori), and a multi-cloning site that is situated between the two mosaic ends (ME) that Tn5 transposase interacts with. The first step in the construction of pMOD-Linker was to remove the original multi-cloning site in pMOD2-<MCS> and replace it with a new multi-cloning site that has unique restriction sites for AsiSi, FseI and SbfI. This was done by cutting the plasmid with EcoRI and HindIII and purifying the large (about 2.5 Kbp) vector fragment by agarose gel electrophoresis. The new multi-cloning site was then generated by annealing together two synthetic oligonucleotides, Linker B (SEQ ID NO:35) and Linker T (SEQ ID NO:36) that were both phosphorylated at their 5' end.

```
Linker B:
                                        (SEQ ID NO: 35)
aattCTACCTGCAGGAGTAGGCCGGCCATGAGCGATCGCA Linker T:
                                        (SEQ ID NO: 36)
agctTGCGATCGCTCATGGCCGGCCTACTCCTGCAGGTAG
```

These oligonucleotides are complimentary to each other, and when annealed together form a double stranded linker that has single-stranded overhangs at both ends (lower case letters), which allow the DNA fragment to be ligated between the EcoRI and HindIII sites of the large pMOD™-2<MCS> vector fragment described above. As noted above this synthetic linker also contains three unique restriction sites (AsiSi, FseI and SbfI) that can be used for subsequent cloning steps. The SbfI site is underlined with a thin line, the FseI site is underlined with a thick line and the AsiSi site is underlined with two thin lines. Linker B and Linker T were annealed together and the resulting DNA fragment was inserted between the EcoRI and HindIII sites of pMOD™-2<MCS> in a standard ligation reaction. The ligation reaction mixture was used to transform E. coli DH10B and the transformed cells were plated on LB media that contained 100 μg/ml of ampicillin. Plasmid DNA was then isolated from a representative ampicillin-resistant colony that contained the new multi-cloning site. A circle diagram of the resulting plasmid construct (referred to below as "pMOD-Linker") is shown in FIG. 7B.

Construction of pMOD-Linker-Spec

A DNA fragment that confers resistance to spectinomycin (Spec$^r$) and has a wild type loxP site at both ends was inserted between the AsiSi and FseI sites of the pMOD-Linker construct described above. The source of the loxP-flanked Spec$^r$ cassette was plasmid pLDHSp-9WW (FIG. 8), which is described in great detail in U.S. application Ser. No. 11/862,566. In the first step, MOD-Linker plasmid DNA was sequentially digested with FseI and AsiSI, and the large vector fragment was purified using a DNA Clean & Concentrator™-5 spin column kit that was purchased from Zymo Research Corporation (Cat. No. D04003). Next, plasmid pLDHSp-9WW was also double-digested with the same two enzymes and the small (about 1.1 Kbp) DNA fragment that contained the loxP-flanked Spec$^r$ cassette was purified by agarose gel electrophoresis. The two DNA fragments of interest were then ligated together, and the transformation reaction mixture was introduced into E. coli DH10B using electroporation. Transformants were plated on LB media that contained ampicillin (100 μg/ml) and spectinomycin (100 μg/ml) and growth was at 37° C. Plasmid DNA was then isolated from one of the ampicillin-resistant colonies that contained a DNA fragment with the correct size and this was used for subsequent manipulations. A circle diagram of this construct (referred to below as "pMOD-Linker-Spec") is shown in FIG. 7C.

Construction of pMOD-Linker-Spec-801GapXylA and pMOD-Linker-Spec-641GapXylA

A DNA fragment that contains the entire Pgap, the XylA coding region, and the stem-loop region that is between the XylA and XylB open reading frames was PCR-amplified from ZW801-4 using Primers 3 and 4 (SEQ ID NOs:37 and 38, respectively) and resuspended cells as a template. As already noted, DNA sequence analysis has shown that ZW801-4 has the same G->T point mutation at position -189 in the Pgap promoter that drives the expression of the integrated E. coli XylA/B operon as ZW658 and that the Pgap in both strains are identical.

```
Primer 3
                                        (SEQ ID NO: 37)
TCACTCATggccggccGTTCGATCAACAACCCGAATCC Primer 4
                                        (SEQ ID NO: 38)
CTACTCATcctgcaggCCGATATACTTATCGATCGTTCC
```

The underlined bases of Primer 3 (forward primer) hybridize to the first 22 bases of the Pgap (and to nts 316-337 of SEQ ID NO:34, while the lower case letters correspond to an FseI site that was added to the 5' end of the primer. The underlined bases of Primer 4 (reverse primer) hybridize just downstream from the stem-loop region that is after the XylA stop codon (and to the last 12 nts of SEQ ID NO:34), while the lower case letters correspond to an SbfI site that was added to the 5' end of the primer.

The PCR product was double-digested with FseI and SbfI, and purified using a DNA Clean & Concentrator™-5 spin column kit that was purchased from Zymo Research Corporation (Cat. No. D04003). Next, plasmid pMOD-Linker-Spec was cut with the same two enzymes and the resulting large vector fragment was purified using the same procedure. The two DNA fragments of interest were then ligated together, and the transformation reaction mixture was introduced into E. coli DH10B using electroporation. The cells were plated on LB media that contained ampicillin (100 μg/ml) and spectinomycin (100 μg/ml) and growth was at 37° C. Transformants that contained a plasmid with a correct size insert were identified by PCR using Primers 3 and 4 and resuspended colonies as a template ("colony PCR"). The plasmid that was selected for further manipulation is referred to below as pMOD-Linker-Spec-801GapXylA, and a circle diagram of this construct is shown in FIG. 9.

The same steps described above were used to generate another plasmid that is referred to below as "pMOD-Linker-Spec-641GapXylA", except the template that was used for PCR-amplification of the Pgap-XylA gene DNA fragment was a cell suspension of ZW641. pMOD-Linker-Spec-641GapXylA and pMOD-Linker-Spec-801 GapXylA are identical except for the G->T substitution in the Pgap that distinguishes ZW658 (and ZW801-4) from ZW641.

Construction of pZB188-aadA-801GapXylA

As described in the first paragraph of Example 6, pZB188-aadA-801GapXylA is an E. coli Xylose Isomerase expression vector for Z. mobilis that is identical to pZB188-aadA-641GapXylA, but it has the same G->T substitution in the Pgap that drives expression of the integrated Pgap-XylA/B operon in ZW658 (and ZW801-4). To construct this plasmid, pMOD-Linker-Spec-801GapXylA (FIG. 10A) was double digested with MluI and SalI and the smaller DNA fragment (about 1100 bp) was purified using agarose gel electrophoresis and the Zymoclean Gel DNA Recovery Kit (catalog #D4001, Zymo Research). This fragment contains the Pgap G->T substitution and part of the XylA ORF and was used to replace the corresponding fragment in pZB188-aadA-641GapXylA (FIG. 10B), after cutting the latter construct with the same two enzymes and purifying the large vector fragment by agarose gel electrophoresis. The two fragments of interest were then ligated together and the ligation reaction mixture was introduced into E. coli DH10B using electroporation. Transformants were plated on LB media that contained spectinomycin (100 μg/ml) and growth was at 37° C.

Figure 10C:
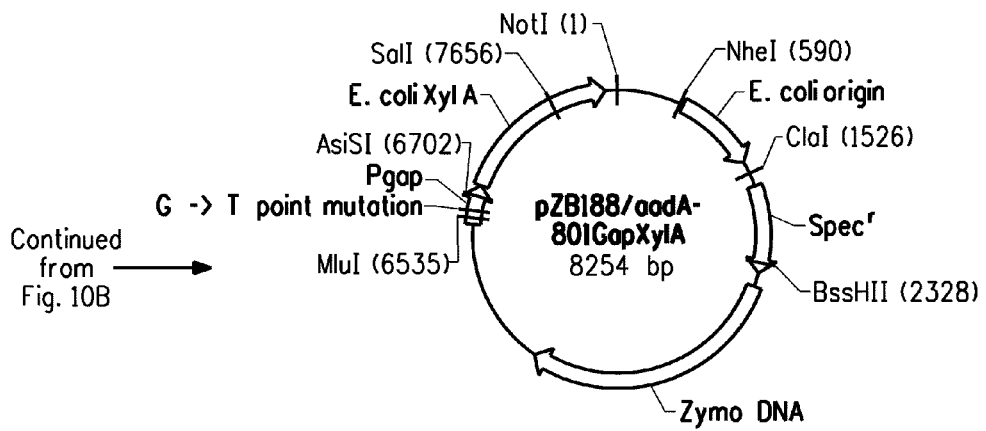

Plasmid DNA was isolated from a spectinomycin-resistant colony and the presence of the Pgap promoter G->T substitution was confirmed by DNA sequence analysis. The plasmid used for subsequent manipulations, ("pZB188-aadA-801GapXylA") is shown in FIG. 10C.

Example 7

Overexpression of E. coli Xylose Isomerase in ZW641

The enzyme activity measurements in Table I show that xylose isomerase and xylulokinase activities increased dramatically during the transition from ZW641 to ZW658. To test the hypothesis that xylose isomerase is the rate-limiting enzyme for growth on xylose in ZW641, the enzyme was overexpressed in this strain using the multicopy plasmid, pZB188/aadA-641GapXylA (FIG. 6C). The control for this experiment was ZW641 transformed with the multicopy plasmid pZB188/aadA, which lacks the Pgap-E. coli xylose isomerase expression cassette (FIG. 6B). The construction of both of these plasmids is described in Example 5, and the transformation protocol was essentially as described in Example 5 of commonly owned and co-pending U.S. App. Pub. No. US20080187973. Briefly, non-methylated plasmid DNA (isolated from E. coli SSC110, which is a dcm⁻ and dam⁻ strain) was introduced into ZW641 using electroporation, and the transformed cells were plated on LB media that contained 200 µg/ml spectinomycin. After a 48-hr growth period at 30° C. under anaerobic conditions, three primary transformants were randomly selected for each plasmid, and these were patched (transferred) onto agar plates that contained the same growth media for further characterization.

FIG. 11 shows growth curves (OD600 versus time) in xylose-containing media for the three strains that harbored the 641Pgap-E. coli xylose isomerase expression plasmid (X1, X2 and X2) and the three strains that harbored the control plasmid (C1, C2 and C3). This experiment was performed at 30° C. in shake flasks (5-ml cultures in 15-ml tubes at 150 rpm), and the growth media was mRM3-X10 (10 g/L yeast extract, 2 g/L KH2PO4, 1 g/L MgSO4 and 100 g/L xylose) that also contained spectinomycin (200 µg/ml). The cultures were started with a loop of cells from the patched plate described in the above paragraph and the initial OD600 in each case was about 0.13. Similar to ZW641, the three strains with the control plasmid barely grew on xylose. In marked contrast, both the rate and extent of growth (final OD600 values) on xylose were dramatically improved when ZW641 was transformed with the 641Pgap-E. coli xylose isomerase expression plasmid, pZB188/aadA-641GapXylA. Since all three strains that had this plasmid behaved the same in the experiment that is shown in FIG. 11, only the X1 strain and C1 strain were subjected to further characterization.

Figure 12A:
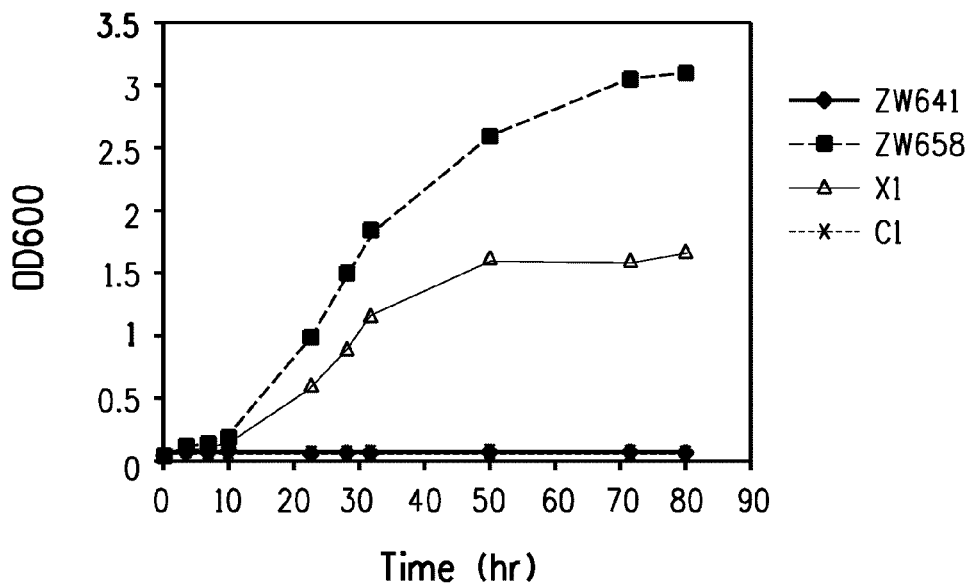
Figure 12B:
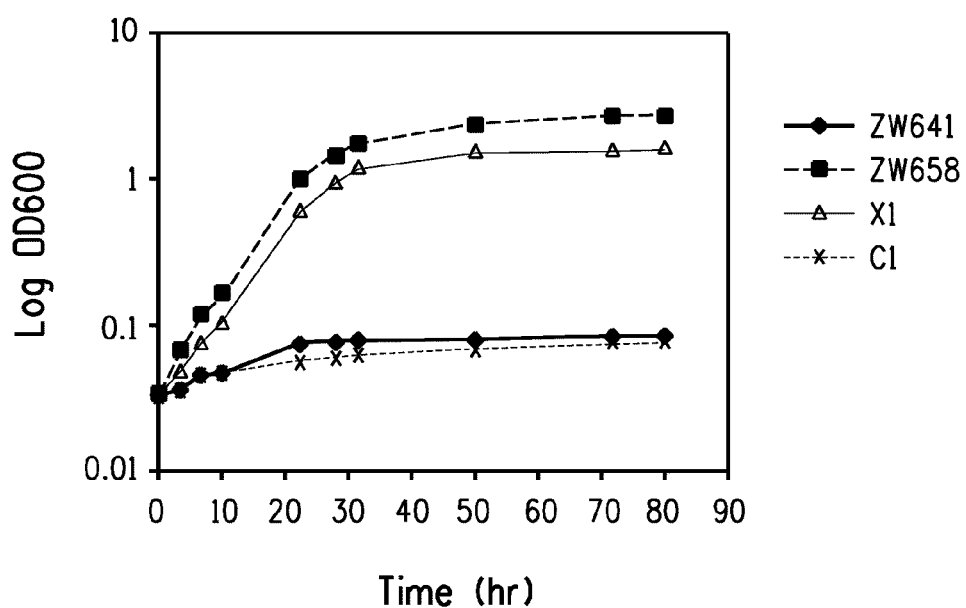

FIG. 12 shows a side-by-side comparison of ZW641, ZW658, X1 and C1 in the same xylose containing growth media without spectinomycin. The conditions for this experiment were identical to those described above but the 20-ml cultures were grown in 50-ml tubes and the initial OD600s were about 4-fold lower (0.035). The growth curves shown in FIG. 12A are plotted on a linear scale (OD600 versus Time), while FIG. 12B shows the same experimental data plotted on a logarithmic scale (log OD600 versus Time) in order to compare exponential growth rates. It is apparent from this experiment that the exponential growth rate of X1 is almost as fast as the xylose-adapted strain ZW658, and that this strain grows much better on xylose than the parent strain ZW641 with or without the control plasmid. Thus, high expression of xylose isomerase in ZW641 (driven by a 641Pgap promoter from a multicopy plasmid) has a similar effect on growth on xylose as the increase in xylose isomerase activity had on ZW658 (shown in Table 1). Although the final biomass yield for X1 is about 2-fold lower than that obtained with ZW658, it is clear from this data that the rate-limiting enzyme for growth on xylose in ZW641 is xylose isomerase. The experiments shown in FIGS. 11 and 12 further suggest two other interesting possibilities: (1) that the large increase in xylose isomerase activity that occurred during the transition from ZW641 to ZW658 (Table I) was largely responsible for the better growth on xylose that occurred during the "xylose adaptation" process; and (2) that the increase in xylose isomerase activity might have resulted from the G->T substitution in the Pgap promoter that drives expression of the chromosomally-integrated Pgap-XylA/B operon that is present in ZW658.

Example 8

Transposon-Mediated Integration of E. coli Xylose Isomerase in ZW641

ZW641 and two plasmid constructs (pMOD-Linker-Spec-801GapXylA and pMOD-Linker-Spec-641GapXylA) were used to test the hypothesis that the Pgap promoter with the G->T substitution that drives expression of the integrated XylA/B operon in ZW658 (henceforth referred to as the "801GAP promoter") is stronger than the corresponding promoter in ZW641 (henceforth referred to as the "641GAP promoter"). ZW641 was selected for these experiments since it's barely able to grow on xylose, and because overexpression of xylose isomerase in this strain results in faster growth on xylose (Example 7, FIGS. 11 and 12). The basic idea was to introduce an extra copy of the E. coli xylose isomerase gene (driven by the 641GAP promoter or the 801GAP promoter) into the chromosome of ZW641 and see which construct would result in the fastest growth on xylose. Chromosomal integration of the two chimeric genes was accomplished using Epicentre's transposome technology.

As already indicated, pMOD-Linker-Spec-641GapXylA and pMOD-Linker-Spec-801GapXylA are identical plasmids except for the G->T point mutation that is present in the Pgap promoter in the latter construct. The transposable element used for random insertion into DNA in both cases consisted of the two 19-bp mosaic ends (MEs) and the entire DNA fragment that is sandwiched between them. As shown in FIG. 9, this element, which is referred to as the transposon, contains a spectinomycin-resistance cassette (Spec$^r$) and a downstream Pgap-E. coli xylose isomerase expression cassette. The protocol that was used to form the transposomes was essentially the same as that described in Epicentre's instruction manual for the EZ::TN™ pMOD™-2<MCS> Transposon Construction Vector (Cat. No. MOD0602). The 8-µL reaction contained 1.5 µL of 5'-phosphorylated, blunt-ended transposon DNA that was free of Mg⁺⁺ ions (about 250 ng/µL), 4 µL of Epicentre's EZ::TN Transposase and 2.5 µL of 80% (v/v) glycerol. The control transposome reaction mixture was identical but 4 µL of sterile water was substituted for the transposase. The reactions were incubated at room temperature for 30 min and were then transferred to 4° C. for a 2- to 7-day incubation period that is required for the slow isomerization step, which results in the formation of the active transposome; using this procedure the transposomes are stable for at least 3 months at −20° C.

The transposomes were electroporated into ZW641 essentially using the same transformation protocol that is described in U.S. Pat. No. 5,514,583. Briefly, the 40-μL transformation reactions contained about $10^{10}$ cells/ml in 10% (v/v) glycerol, 1 μL of Epicentre's TypeOne™ Restriction Inhibitor (Cat. No. TYO261H) and 1 μL of the control or transposome reaction mixture. The settings for the electroporator were 1.6 kv/cm, 200Ω, and 25 μF, and the gap width of the cuvette was 0.1 cm. Following electroporation, the transformation reactions were diluted with 1.0 ml of MMG media (50 g/L glucose, 10 g/L yeast extract, 5 g/L of tryptone, 2.5 g/L of $(NH_4)_2SO_4$, 0.2 g/L $K_2HPO_4$, and 1 mM $MgSO_4$) and the cells were allowed to recover for about 3 hours at 30° C. The cells were then harvested by centrifugation at room temperature (13,000×g, 5 min) in sterile 1.5-ml microfuge tubes and the supernatant was carefully removed. Cell pellets were resuspended in 200 μL of liquid MMG media and a 100-μL aliquot of each cell suspension was plated on MMG media that contained 1.5% agar and 200 μg/ml of spectinomycin. After a 72-hr incubation period at 30° C. under anaerobic conditions, 3 colonies were on the control plate, 13 colonies were on the 641GapXylA transposome plate and 18 colonies were on the 801GapXylA transposome plate. Six colonies from both transposome plates were randomly selected for further characterization, and these were patched onto agar plates that contained MMX media and 200 μg/ml of spectinomycin; the growth conditions were as described above. MMX media is the same as MMG media, but contains 50 g/L of xylose instead of glucose. After a second round of growth on a fresh MMX plus spectinomycin plate, the six strains that grew the best on xylose (three for each transposome) were used for the experiment described below.

Figure 13A:
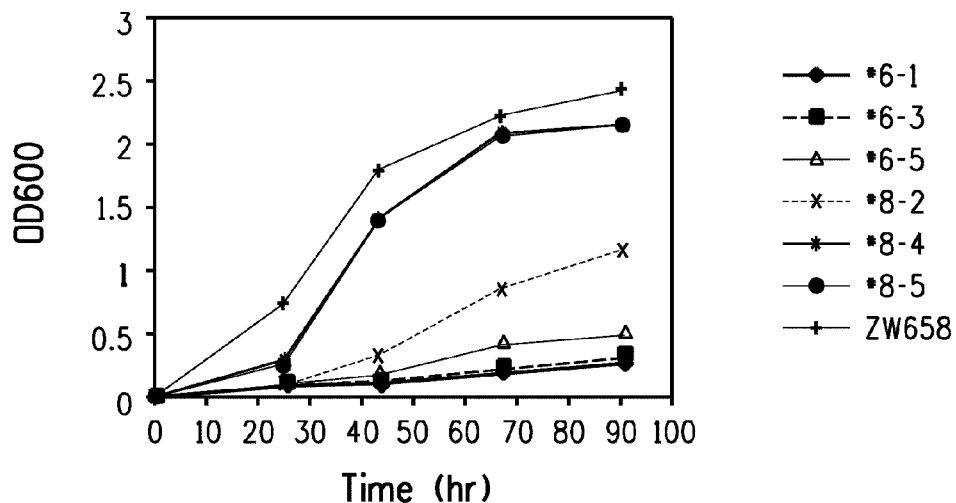

FIG. 13A shows linear growth curves for the three ZW641 strains that were obtained with the 641Gap-XylA transposome (#6-1, #6-3 and #6-5) and the three that received the 801Gap XylA transposome (#8-2, #8-4 and #8-5) in xylose-containing media. The same data is plotted on a log scale in FIG. 13B. This experiment was performed at 30° C. in shake flasks (7-ml cultures in 15-ml tubes at 150 rpm), and mRM3-X10 (10 g/L yeast extract, 2 g/L KH2PO4, 1 g/L MgSO4 and 100 g/L xylose) was the growth media. The cultures were started with a loop of cells from the patched plate described above and the initial ODs were very similar (about 0.02-0.03). The control for this experiment was the xylose-adapted strain ZW658, which has the G->T substitution in the Pgap that drives the chromosomally-integrated E. coli XylA/B operon.

Figure 13B:
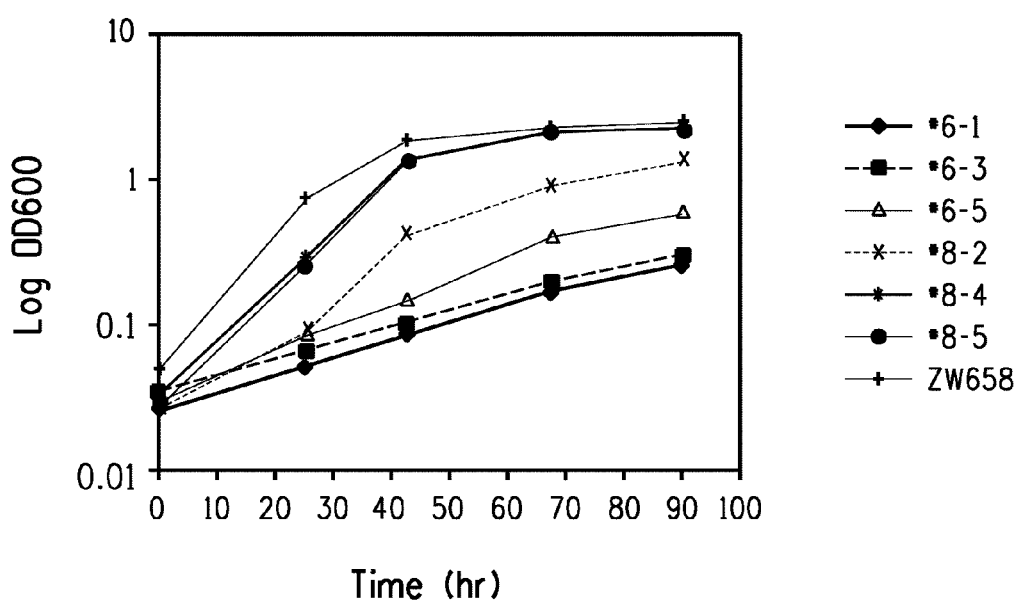

Similar to the parent strain (ZW641) the three strains that had an extra chromosomally-integrated copy of the 641GapXylA expression cassette grew very poorly in xylose-containing media, although it was apparent that there were some minor improvements in both the growth rate and biomass yield (OD600), especially for strain #6-5 (compare FIG. 12A and FIG. 13A). In contrast, all three of the strains that were obtained with the 801GapXylA transposon grew much better on xylose than the parent strain (FIGS. 13A and 13B). In fact, two of the transformants (#8-4 and #8-5) grew almost as well on this sugar as ZW658 and the ZW641 transformants that harbored the multi-copy plasmid pZB188/aadA-GapXylA, which contains a 641GapXylA expression cassette (compare FIG. 12 and FIG. 13). Since transposition is a random event and all six strains have the 641GapXylA or 801GapXylA expression cassette inserted at different locations in the chromosome, differences in foreign gene expression that were observed in this experiment using the same transposome are likely to be due to positional effects. For example, position effects may account for the better growth of #6-5 than of #6-1 and #6-3, and for the poorer growth of #8-2 than of #8-4 and #8-5. Nevertheless, despite the small size of the population that was analyzed, the results that are shown in FIG. 13 strongly support the notion that the G->T mutation that is present in the Pgap promoter that drives the E. coli XylA/B operon in ZW658 and ZW801-4 is responsible for the higher xylose isomerase activity and better growth on xylose that is observed with these strains, compared to the parent strain ZW641.

Example 9

The 801GAP Promoter Directs Higher Expression Levels of Ribose 5-Phosphate Isomerase in Z. mobilis than the 641GAP Promoter If the 801GAP promoter is really stronger than the 641GAP promoter, its stimulatory effect on expression should not be restricted to the E. coli xylose isomerase gene, and enhanced expression of other proteins with this promoter would also be expected. To address this important issue, the Z. mobilis gene that codes for ribose 5-phosphate isomerase (RPI) was fused to both promoters, and the chimeric genes were inserted into a multi-copy plasmid that replicates in Z. mobilis. The resulting Pgap-RPI expression plasmids (pZB188/aadA-641GapRPI and pZB188/aadA-801GapRPI) were introduced into Z. mobilis and RPI expression levels were analyzed by SDS-PAGE as described below.

Construction of pZB188aadA/Gap/Zymo RPI/*EcoliSL*

Plasmid pZB188aadA/Gap/Zymo RPI/*EcoliSL* was an important intermediate in the construction of the two Pgap-RPI expression plasmids that were used in the present invention. As shown in FIG. 14, this plasmid contains an expression cassette for the Z. mobilis ribose 5-phosphate isomerase (RPI) gene that is located between the unique NcoI and XhoI sites. An overlap PCR technique described below was used to generate the RPI expression cassette, which is a chimeric gene that contains the full-length 641GAP promoter sequence (nts 316-619 of SEQ ID NO:34) and the entire open reading frame of the Z. mobilis RPI gene. The RPI ORF corresponds to nts 1224730-1225203 of the Z. mobilis genome (GenBank accession number AE008692), and the initiation codon of RPI is directly fused to the 3'-end of the 641GAP promoter.

The template for the 641Gap promoter was pZB188/aadA-641GapXylA, and a 320-bp DNA fragment was amplified from this plasmid using Primers 5 and 6 (SEQ ID NOs:39 and 40, respectively) in a PCR reaction. The resulting PCR product contains the 641GAP promoter and the first 15 bp of the Z. mobilis RPI ORF that are attached to its 3'-end starting with the GTG initiation codon. This fragment also has a unique NcoI site at its 5'-end (lower case letters) that was added to the 5'-end of Primer 5 for cloning purposes.

```
Primer 5
                                      (SEQ ID NO: 39)
CATGccatggGAGCTCGTTCGATCAACAACCCGAATCCTA Primer 6
                                      (SEQ ID NO: 40)
CACAGCAGAGGTCACGTTTATTCTCCTAACTTATTAAGTAGC
```

In a separate PCR reaction, Primers 7 and 8 (SEQ ID NOs:41 and 42, respectively) were used to generate a 473-bp fragment that contains the entire ORF of the native Z. mobilis RPI gene. The template that was used for amplification was genomic DNA that was isolated from the Z. mobilis strain ZW801-4. Note that the 5'-end of Primer 7 has 15 bp of an overlap sequence that can hybridize to the 3'-end of the 320-bp 641 GAP promoter fragment, and that an XhoI site (lower case letters) was added to the 5'-end of Primer 8 for cloning purposes.

```
Primer 7
                                               (SEQ ID NO: 41)
GTTAGGAGAATAAACGTGACCTCTGCTGTGCCATCAAA Primer 8
                                               (SEQ ID NO: 42)
CCGctcgagCTAGATATTGAACTGAGGATTCGAAA
```

The two fragments described above were then subjected to an overlap PCR reaction using Primers 5 and 8 (SEQ ID NOs:39 and 42, respectively), and this manipulation resulted in the generation of the RPI expression cassette. The latter is a 778-bp fragment that contains the 641GAP promoter fused directly to the start codon of the Z. mobilis RPI ORF. The PCR product was then cut with NcoI and XhoI, and the resulting fragment was inserted into the NcoI and XhoI sites of a plasmid that was ultimately derived from pZB188/aada-641GapXylA (FIG. 6C) to yield the final product pZB188aadA/Gap/Zymo RPI/EcoliSL (FIG. 14). It is important to note that this plasmid, which is an RPI expression vector for Z. mobilis, also contains the stem-loop region that is present in the intergenic region of the E. coli XylA/B operon, and that this stabilizing element is located between the XhoI and NotI sites just downstream from the RPI stop codon. The nucleotide sequence of the RPI expression cassette that is in plasmid pZB188aadA/Gap/Zymo RPI/EcoliSL (including the XylA stem-loop structure) is disclosed in SEQ ID NO:43. The nucleotide sequence that is shown corresponds to the DNA fragment that is located between the NcoI and NotI sites, and includes both restriction sites.

Figure 15A:
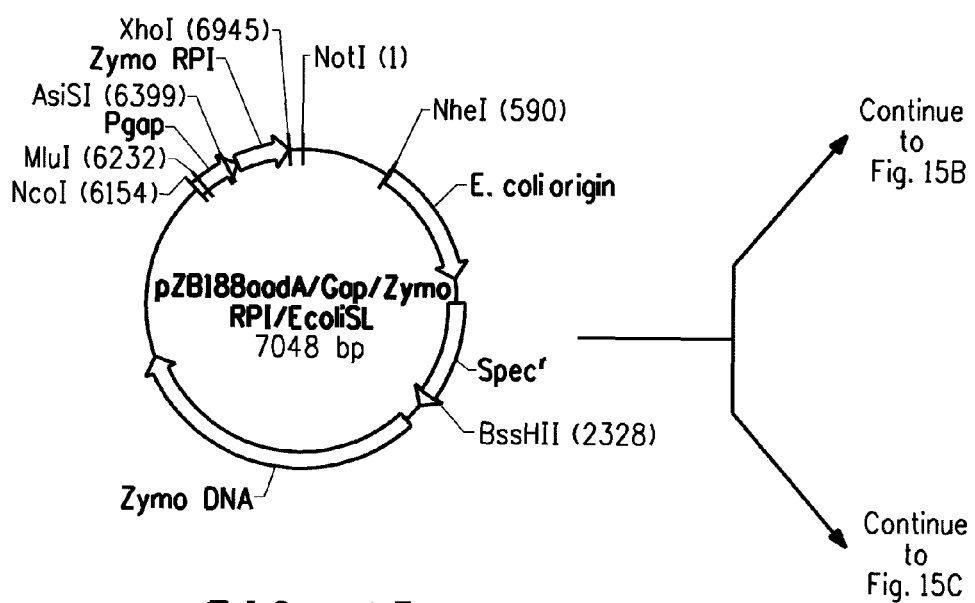
Figure 15C:
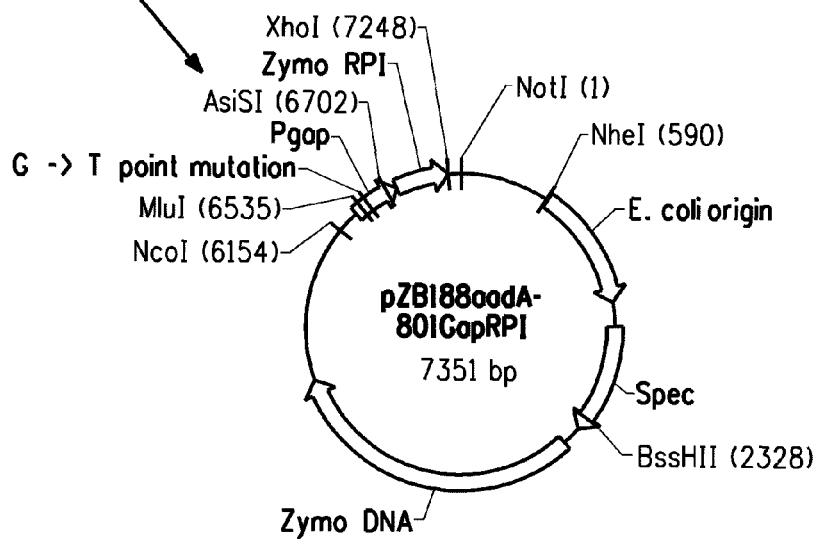

Construction of pZB188/aadA-641GapRPI and pZB188/aadA-801GapRPI pZB188/aadA-641GapRPI and pZB188/aadA-801GapRPI are Pgap-RPI expression plasmids for Z. mobilis that are identical, except the latter construct has the G->T substitution that distinguishes the 801GAP promoter from the 641GAP promoter. A 1240-bp DNA fragment that originated from pZB188aadA/Gap/Zymo RPI/EcoliSL was used to convert pZB188/aadA-641GapXylA (FIG. 6C) to pZB188/aadA-641GapRPI (FIG. 15B) and pZB188/aadA-801GapXylA (FIG. 10C) to pZB188/aadA-801GapRPI (FIG. 15C). This piece of DNA was generated by cutting pZB188aadA/Gap/Zymo RPI/EcoliSL with AsiSI and NheI, and purifying the smaller fragment by agarose gel electrophoresis. As shown in FIG. 15A, pZB188aadA/Gap/Zymo RPI/EcoliSL has unique AsiSI and NheI restriction sites, and the same sites are also present in pZB188/aadA-641GapXylA and pZB188/aadA-801GapXylA. Note that AsiSI cleaves all three of these plasmids in the Pgap downstream from the G->T substitution that distinguishes the 801GAP promoter from the 641GAP promoter, and that NheI cuts the plasmid backbone about 700 bp downstream from the XylA or RPI stop codons. The 1240-bp DNA fragment that was obtained from pZB188aadA/Gap/Zymo RPI/EcoliSL therefore contains a small stretch of DNA that the 641Gap promoter and 801Gap promoter share in common, the entire RPI open reading frame and the stabilizing XylA stem-loop region.

In the next step in the construction of pZB188/aadA-641GapRPI and pZB188/aadA-801GapRPI, the 1240-bp DNA fragment described above was inserted between the AsiSI and NheI sites in pZB188/aadA-641GapXylA and pZB188/aadA-801GapXylA in two separate ligation reactions, after cutting both of these plasmids with AsiSI and NheI and purifying the larger vector fragments. Both ligation reaction mixtures were introduced into E. coli DH10B using electroporation, and transformants were plated on LB media that contained spectinomycin (100 μg/ml); growth was at 37° C. Finally, pZB188/aadA-641GapRPI (FIG. 15B) and pZB188/aadA-801GapRPI (FIG. 15C) plasmid DNA was isolated from colonies that contained the correct construct (as confirmed by DNA sequence analysis), and both plasmids were then introduced into E. coli SCS110 (dam⁻, dcm⁻) to generate non-methylated plasmid DNA for transformation of Z. mobilis.

Expression of RPI with the 641GAP Promoter and the 801GAP Promoter

The two Pgap-RPI expression vectors described above (pZB188/aadA-641GapRPI and pZB188/aadA-801GapRPI) were introduced into the wild type Z. mobilis strain ZW1 using electroporation and non-methylated plasmid DNA. The transformed cells were grown anaerobically at 30° C. on 1.5% agar plates that contained MMG media (50 g/L glucose, 10 g/L yeast extract, 5 g/L of tryptone, 2.5 g/L of $(NH_4)_2SO_4$, 0.2 g/L $K_2HPO_4$, and 1 mM $MgSO_4$) and 200 μg/ml of spectinomycin. Two randomly selected colonies that contained the 641GAP-RPI plasmid (641gapRpi #1 and 641gapRpi #2) and two that harbored the 801GAP-RPI plasmid (801gapRpi #1 and 801gapRpi #2) were patched onto a 1.5% agar plate that contained the same growth media, and the plate was incubated for about 24 hr at 30° C. under anaerobic conditions. This plate was used to start seed cultures for the RPI expression experiment.

The seed cultures were started with a loop of cells and were grown at 30° C. (150 rpm) in 15-ml capped tubes that contained 5 ml of MMG media and spectinomycin (200 μg/ml). The control for this experiment (the parent strain, ZW1) was grown under the same conditions, but the growth media lacked spectinomycin. The seed cultures were allowed to reach saturation, and were then used to start 20-ml cultures in 50-ml capped tubes, using the same growth media and conditions described above. The initial OD600 values were about 0.12 in all cases. Aliquots of the cultures (500-μL) were harvested during the exponential phase (OD600 about 1.1) by centrifugation (15,000×g, 10 min), and the cell pellets were resuspended in 250 μL of 1×SDS-PAGE sample buffer. All reagents for electrophoresis were obtained from Invitrogen. One milliliter of 1×SDS-PAGE sample buffer contains 250 μL NuPAGE™ LDS 4× Sample Buffer (Cat. No. N0007), 100 μL NuPAGE™ Sample Reducing Agent (Cat. No. NP0004) and 650 μL distilled water. The samples were heated for 10 min at 80° C., and particulate debris was removed by centrifugation (15,000×g, 10 min). Aliquots of the clarified samples (20 μL) were then subjected to SDS-PAGE, using a NuPAGE™ 12% Bis-Tris gel (Cat. No. NP0341) and the NuPAGE™ MES SDS Running Buffer (Cat. No. NP0002) protocol for reduced samples as recommended by the vendor. The gel was run at room temperature at constant voltage (180 V) for about 1 hr and was stained with Invitrogen SimplyBlue SafeStain (Cat. No. LC6060) as recommended by the manufacturer.

The molecular mass of the Z. mobilis RPI protein is 16927.37 Da based on the DNA sequence of the open reading frame. As shown in FIG. 16, several lightly stained protein bands migrated in the polyacrylamide gel in this region (i.e. between the 17 kDa and 19 kDa molecular weight standards) for the parent strain, ZW1 (Lanes 2 and 7). Visual inspection of the gel revealed that the intensity of one of the stained bands (indicated with an arrow) increased at least 2-fold when the 641GAP-RPI expression plasmid was introduced into ZW1 (Lanes 3 and 5), indicating that this is the RPI protein. Furthermore, it is quite evident in FIG. 12 that the intensity of the Z. mobilis RPI band increased far more dramatically for the two strains that harbored the 801GAP-RPI expression plasmid (Lanes 4 and 6). These results provide compelling evidence that the 801GAP promoter is a stronger promoter than the 648GAP promoter, and that the latter is useful tool for expressing foreign genes at very high levels.

Example 10

Enzyme Activity and Sequence Comparison the Transgene GAP Promoter Regions of Independently Adapted Strains of Xylose Utilizing *Z. mobilis*

Since strain 8b (Example 1 and US App. Pub. No. 20030162271) was obtained using a similar course of gene introduction and strain adaptation as was ZW658, the transgene activities of the pentose phosphate pathway and the sequence of the PgapxylAB operon were also compared in partially and more fully adapted strains of this independent strain production. Enzyme activities for products of the PgapxylAB operon in a partially adapted strain 8XL4 and the final adapted strain 8b were measured using the techniques described in General Methods and the results expressed as µmoles product/mg protein/minute are shown in Table 2.

TABLE 2

Enzyme activities in different xylose-utilizing adapted *Z. mobilis* strains

| Strain | Xylose isomerase | Xyulose kinase |
|--------|------------------|----------------|
| 8XL4   | 0.027 +/− 0.004  | 1.10 +/− 0.41  |
| 8b     | 0.142 +/− 0.057  | 5.76 +/− 0.43  |

As with the adaptation that occurred when the strains preceding ZW658 picked up mutations that allowed enhanced growth on xylose, strain 8b had increased activity for products of both genes in the xylAB operon over its predecessor strain 8XL4. Once again the increase in measured enzyme activity was about five fold increased over the less adapted strain.

The Pgap directing expression of the xylAB operon was sequenced in the 8b and 8XL4 strains. A PCR fragment was prepared using a forward PCR primer (GAP-F8; SEQ ID NO:44) from the 5' end of the promoter and a reverse primer from the xylA coding region (XylAB851R; SEQ ID NO:5). The resulting PCR product was sequenced using primers GAP-F8, XylAB449R, and XylAB851R (SEQ ID NOs:44, 46, and 45). The promoter sequence from ZW8XL4 is given in SEQ ID NO:3 and that from 8b in SEQ ID NO:5. These promoter sequences also both had the one difference with the published sequence of the Pgap of strain CP4 as in the Pgap of the xylAB operon in ZW641 and ZW658. In addition to these common changes there was also a single base pair difference between the ZW641 and ZW658 Pgap sequences. While the G to T change at −189 to the start ATG was not present in the comparison of 8XL4 and 8b, a C to T change did occur at position −89 with respect to the start ATG.

As with the promoter sequence of the PgapxylAB operon in strain ZW658, the promoter sequence of the PgapxylAB operon in strain 8b changed during adaptation to a new sequence which allowed production of more of the protein from the coding regions under its control than did the sequence of the same promoter from the partially adapted strain.

What is claimed is:

1. An isolated nucleic acid molecule comprising a Z. mobilis glyceraldehyde-3-phosphate dehydrogenase gene promoter that has a base substitution in a position selected from the group consisting of position 116, position 217, or both positions 116 and 217; wherein the position numbers are of SEQ ID NO:1; and wherein at position 116 a T replaces G, and at position 217 a T replaces C.

2. The isolated nucleic acid molecule of claim 1 comprising a sequence selected from the group consisting of SEQ ID NO:4, 5, 6, 7, 8 9, 10, 11, and 12.

3. A chimeric gene comprising the isolated nucleic acid molecule of claim 1 operably linked to a heterologous nucleic acid molecule.

4. The chimeric gene of claim 3 wherein the heterologous nucleic acid molecule encodes a protein or peptide.

5. The chimeric gene of claim 3 wherein the heterologous nucleic acid molecule codes for a regulatory RNA molecule selected from the group consisting of an antisense RNA, a ribozyme, and an interfering RNA.

6. A vector comprising the isolated nucleic acid molecule of claim 1.

7. A vector comprising the isolated nucleic acid molecule of claim 2.

8. A method of transforming a bacterial cell selected from the group consisting of *Zymomonas* cells and *Zymobacter* cells comprising introducing into the cell the isolated nucleic acid molecule of claim 1.

9. A method of transforming a bacterial cell selected from the group consisting of *Zymomonas* cells and *Zymobacter* cells comprising introducing into the cell the isolated nucleic acid molecule of claim 2.

10. The method according to claim 8 wherein introducing comprises integrating the isolated nucleic acid molecule into the genome of the cell or maintaining on a stably replicating plasmid within the cell.

* * * * *

SEQUENCE LISTING

```
<160> NUMBER OF SEQ ID NOS: 48

<210> SEQ ID NO 1
<211> LENGTH: 305
<212> TYPE: DNA
<213> ORGANISM: Zymomonas mobilis

<400> SEQUENCE: 1
gttcgatcaa caacccgaat cctatcgtaa tgatgttttg cccgatcagc ctcaatcgac      60
aattttacgc gtttcgatcg aagcagggac gacaattggc tgggaacggt atactggaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
taagtcggca cgttaaaaaa tagctatgga atataatagc tacttaataa gttaggagaa     300
taaac                                                                305

<210> SEQ ID NO 2
<211> LENGTH: 305
<212> TYPE: DNA
<213> ORGANISM: Zymomonas mobilis

<400> SEQUENCE: 2
gttcgatcaa caacccgaat cctatcgtaa tgatgttttg cccgatcagc ctcaatcgac      60
aattttacgc gtttcgatcg aagcagggac gacaattggc tgggaacggt atactggaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
```

```
taagtcggca cgttaaaaaa tagctatgga atatagtagc tacttaataa gttaggagaa      300
taaac                                                                  305

<210> SEQ ID NO 3
<211> LENGTH: 304
<212> TYPE: DNA
<213> ORGANISM: artificial sequence
<220> FEATURE:
<223> OTHER INFORMATION: cloned ZmPgap with mutation

<400> SEQUENCE: 3
gttcgatcaa caacccgaat cctatcgtaa tgatgttttg cccgatcagc ctcaatcgac       60
aattttacgc gtttcgatcg aagcagggac gacaattggc tgggaacggt atactggaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
taagtcggca cgttaaaaaa tagctatgga atataatagc tactaataag ttaggagaat     300
aaac                                                                  304

<210> SEQ ID NO 4
<211> LENGTH: 304
<212> TYPE: DNA
<213> ORGANISM: artificial sequence
<220> FEATURE:
<223> OTHER INFORMATION: mutated promoter

<400> SEQUENCE: 4
gttcgatcaa caacccgaat cctatcgtaa tgatgttttg cccgatcagc ctcaatcgac       60
aattttacgc gtttcgatcg aagcagggac gacaattggc tgggaacggt atacttgaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
taagtcggca cgttaaaaaa tagctatgga atataatagc tactaataag ttaggagaat     300
aaac                                                                  304

<210> SEQ ID NO 5
<211> LENGTH: 304
<212> TYPE: DNA
<213> ORGANISM: artificial sequence
<220> FEATURE:
<223> OTHER INFORMATION: mutant promoter

<400> SEQUENCE: 5
gttcgatcaa caacccgaat cctatcgtaa tgatgttttg cccgatcagc ctcaatcgac       60
aattttacgc gtttcgatcg aagcagggac gacaattggc tgggaacggt atactggaat     120
aaatggtctt cgttatggta ttgatgtttt tggtgcatcg gccccggcga atgatctata     180
tgctcatttc ggcttgaccg cagtcggcat cacgaataag gtgttggccg cgatcgccgg     240
taagtcggca cgttaaaaaa tagctatgga atataatagc tactaataag ttaggagaat     300
aaac                                                                  304

<210> SEQ ID NO 6
<211> LENGTH: 304
<212> TYPE: DNA
<213> ORGANISM: artificial sequence
<220> FEATURE:
<223> OTHER INFORMATION: double mutation promoter

<400> SEQUENCE: 6
```

```
gttcgatcaa caacccgaat cctatcgtaa tgatgttttg cccgatcagc ctcaatcgac      60
aattttacgc gtttcgatcg aagcagggac gacaattggc tgggaacggt atacttgaat     120
aaatggtctt cgttatggta ttgatgtttt tggtgcatcg gccccggcga atgatctata     180
tgctcatttc ggcttgaccg cagtcggcat cacgaataag gtgttggccg cgatcgccgg     240
taagtcggca cgttaaaaaa tagctatgga atataatagc tactaataag ttaggagaat     300
aaac                                                                  304
```

```
<210> SEQ ID NO 7
<211> LENGTH: 305
<212> TYPE: DNA
<213> ORGANISM: artificial sequence
<220> FEATURE:
<223> OTHER INFORMATION: promoter with mutation

<400> SEQUENCE: 7
gttcgatcaa caacccgaat cctatcgtaa tgatgttttg cccgatcagc ctcaatcgac      60
aattttacgc gtttcgatcg aagcagggac gacaattggc tgggaacggt atacttgaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
taagtcggca cgttaaaaaa tagctatgga atataatagc tacttaataa gttaggagaa     300
taaac                                                                 305
```

```
<210> SEQ ID NO 8
<211> LENGTH: 305
<212> TYPE: DNA
<213> ORGANISM: artificial sequence
<220> FEATURE:
<223> OTHER INFORMATION: promoter with mutation

<400> SEQUENCE: 8
gttcgatcaa caacccgaat cctatcgtaa tgatgttttg cccgatcagc ctcaatcgac      60
aattttacgc gtttcgatcg aagcagggac gacaattggc tgggaacggt atactggaat     120
aaatggtctt cgttatggta ttgatgtttt tggtgcatcg gccccggcga atgatctata     180
tgctcatttc ggcttgaccg cagtcggcat cacgaataag gtgttggccg cgatcgccgg     240
taagtcggca cgttaaaaaa tagctatgga atataatagc tacttaataa gttaggagaa     300
taaac                                                                 305
```

```
<210> SEQ ID NO 9
<211> LENGTH: 305
<212> TYPE: DNA
<213> ORGANISM: artificial sequence
<220> FEATURE:
<223> OTHER INFORMATION: promoter with mutations

<400> SEQUENCE: 9
gttcgatcaa caacccgaat cctatcgtaa tgatgttttg cccgatcagc ctcaatcgac      60
aattttacgc gtttcgatcg aagcagggac gacaattggc tgggaacggt atacttgaat     120
aaatggtctt cgttatggta ttgatgtttt tggtgcatcg gccccggcga atgatctata     180
tgctcatttc ggcttgaccg cagtcggcat cacgaataag gtgttggccg cgatcgccgg     240
taagtcggca cgttaaaaaa tagctatgga atataatagc tacttaataa gttaggagaa     300
taaac                                                                 305
```

```
<210> SEQ ID NO 10
```

```
<211> LENGTH: 305
<212> TYPE: DNA
<213> ORGANISM: artificial sequence
<220> FEATURE:
<223> OTHER INFORMATION: promoter with mutation

<400> SEQUENCE: 10
gttcgatcaa caacccgaat cctatcgtaa tgatgttttg cccgatcagc ctcaatcgac    60
aattttacgc gtttcgatcg aagcagggac gacaattggc tgggaacggt atacttgaat   120
aaatggtctt cgttatggta ttgatgtttt tggtgcatcg gccccggcga atgatctata   180
tgctcatttc ggcttgaccg cagtcggcat cacgaacaag gtgttggccg cgatcgccgg   240
taagtcggca cgttaaaaaa tagctatgga atatagtagc tacttaataa gttaggagaa   300
taaac                                                               305

<210> SEQ ID NO 11
<211> LENGTH: 305
<212> TYPE: DNA
<213> ORGANISM: artificial sequence
<220> FEATURE:
<223> OTHER INFORMATION: promoter with mutation

<400> SEQUENCE: 11
gttcgatcaa caacccgaat cctatcgtaa tgatgttttg cccgatcagc ctcaatcgac    60
aattttacgc gtttcgatcg aagcagggac gacaattggc tgggaacggt atactggaat   120
aaatggtctt cgttatggta ttgatgtttt tggtgcatcg gccccggcga atgatctata   180
tgctcatttc ggcttgaccg cagtcggcat cacgaataag gtgttggccg cgatcgccgg   240
taagtcggca cgttaaaaaa tagctatgga atatagtagc tacttaataa gttaggagaa   300
taaac                                                               305

<210> SEQ ID NO 12
<211> LENGTH: 305
<212> TYPE: DNA
<213> ORGANISM: artificial sequence
<220> FEATURE:
<223> OTHER INFORMATION: promoter with mutations

<400> SEQUENCE: 12
gttcgatcaa caacccgaat cctatcgtaa tgatgttttg cccgatcagc ctcaatcgac    60
aattttacgc gtttcgatcg aagcagggac gacaattggc tgggaacggt atacttgaat   120
aaatggtctt cgttatggta ttgatgtttt tggtgcatcg gccccggcga atgatctata   180
tgctcatttc ggcttgaccg cagtcggcat cacgaataag gtgttggccg cgatcgccgg   240
taagtcggca cgttaaaaaa tagctatgga atatagtagc tacttaataa gttaggagaa   300
taaac                                                               305

<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
cgatcaacaa cccgaatcct atcg                                           24

<210> SEQ ID NO 14
<211> LENGTH: 26
<212> TYPE: DNA
```

```
<213> ORGANISM: artificial sequence
<220> FEATURE:
<223> OTHER INFORMATION: primer

<400> SEQUENCE: 14
gccgttattt gtcgaacaga taatgg                                              26

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
tatgggttca gcggcatgag                                                     20

<210> SEQ ID NO 16
<211> LENGTH: 21
<212> TYPE: DNA
<213> ORGANISM: artificial sequence
<220> FEATURE:
<223> OTHER INFORMATION: primer

<400> SEQUENCE: 16
atgggcatga gatccatagc c                                                   21

<210> SEQ ID NO 17
<211> LENGTH: 38
<212> TYPE: DNA
<213> ORGANISM: artificial sequence
<220> FEATURE:
<223> OTHER INFORMATION: primer

<400> SEQUENCE: 17
ctactcattt cctgcaggtg gtaactcatt gcgcgctc                                 38

<210> SEQ ID NO 18
<211> LENGTH: 38
<212> TYPE: DNA
<213> ORGANISM: artificial sequence
<220> FEATURE:
<223> OTHER INFORMATION: primer

<400> SEQUENCE: 18
catcttactg gcgcgccaaa aatctgcggc tgacatac                                 38

<210> SEQ ID NO 19
<211> LENGTH: 56
<212> TYPE: DNA
<213> ORGANISM: artificial sequence
<220> FEATURE:
<223> OTHER INFORMATION: primer

<400> SEQUENCE: 19
actcatttcc atggcgatcg cactatgcgg ccgcaatgta gcacctgaag tcagcc             56

<210> SEQ ID NO 20
<211> LENGTH: 56
<212> TYPE: DNA
<213> ORGANISM: artificial sequence
<220> FEATURE:
<223> OTHER INFORMATION: primer

<400> SEQUENCE: 20
atctcactcc atggccggcc aactattaat taagaattga ttggctccaa ttcttg             56
```

<210> SEQ ID NO 21
<211> LENGTH: 39
<212> TYPE: DNA
<213> ORGANISM: artificial sequence
<220> FEATURE:
<223> OTHER INFORMATION: LoxP site oligonucleotide

<400> SEQUENCE: 21
cgcataactt cgtataatgt atgctatacg aagttatgc                          39

<210> SEQ ID NO 22
<211> LENGTH: 45
<212> TYPE: DNA
<213> ORGANISM: artificial sequence
<220> FEATURE:
<223> OTHER INFORMATION: loxP site oligonucleotide

<400> SEQUENCE: 22
ggccgcataa cttcgtatag catacattat acgaagttat gcgat                   45

<210> SEQ ID NO 23
<211> LENGTH: 43
<212> TYPE: DNA
<213> ORGANISM: artificial sequence
<220> FEATURE:
<223> OTHER INFORMATION: loxP site oligonucleotide

<400> SEQUENCE: 23
taaataactt cgtataatgt atgctatacg aagttatggc cgg                     43

<210> SEQ ID NO 24
<211> LENGTH: 41
<212> TYPE: DNA
<213> ORGANISM: artificial sequence
<220> FEATURE:
<223> OTHER INFORMATION: loxP site oligonucleotide

<400> SEQUENCE: 24
ccataacttc gtatagcata cattatacga agttatttaa t                       41

<210> SEQ ID NO 25
<211> LENGTH: 26
<212> TYPE: DNA
<213> ORGANISM: artificial sequence
<220> FEATURE:
<223> OTHER INFORMATION: primer

<400> SEQUENCE: 25
ataaaagcgg ccgcagcaca ggatga                                        26

<210> SEQ ID NO 26
<211> LENGTH: 26
<212> TYPE: DNA
<213> ORGANISM: artificial sequence
<220> FEATURE:
<223> OTHER INFORMATION: primer

<400> SEQUENCE: 26
ggcgttaatt aaggcaggtc agcaag                                        26

<210> SEQ ID NO 27
<211> LENGTH: 15
<212> TYPE: DNA
<213> ORGANISM: artificial sequence
<220> FEATURE:
<223> OTHER INFORMATION: primer

```
<400> SEQUENCE: 27
gcgtcagctg acgcg                                               15

<210> SEQ ID NO 28
<211> LENGTH: 18
<212> TYPE: DNA
<213> ORGANISM: artificial sequence
<220> FEATURE:
<223> OTHER INFORMATION: primer

<400> SEQUENCE: 28
cacatcgtgg aagcaata                                            18

<210> SEQ ID NO 29
<211> LENGTH: 17
<212> TYPE: DNA
<213> ORGANISM: artificial sequence
<220> FEATURE:
<223> OTHER INFORMATION: primer

<400> SEQUENCE: 29
gccgaaatga gcatata                                             17

<210> SEQ ID NO 30
<211> LENGTH: 15
<212> TYPE: DNA
<213> ORGANISM: artificial sequence
<220> FEATURE:
<223> OTHER INFORMATION: primer

<400> SEQUENCE: 30
gtgccgactt accgg                                               15

<210> SEQ ID NO 31
<211> LENGTH: 16
<212> TYPE: DNA
<213> ORGANISM: artificial sequence
<220> FEATURE:
<223> OTHER INFORMATION: primer

<400> SEQUENCE: 31
tgacggaatg ctaacg                                              16

<210> SEQ ID NO 32
<211> LENGTH: 35
<212> TYPE: DNA
<213> ORGANISM: artificial sequence
<220> FEATURE:
<223> OTHER INFORMATION: primer

<400> SEQUENCE: 32
ctactcattt atcgatggag cacaggatga cgcct                         35

<210> SEQ ID NO 33
<211> LENGTH: 34
<212> TYPE: DNA
<213> ORGANISM: artificial sequence
<220> FEATURE:
<223> OTHER INFORMATION: primer

<400> SEQUENCE: 33
catcttacta cgcgttggca ggtcagcaag tgcc                          34

<210> SEQ ID NO 34
<211> LENGTH: 2013
<212> TYPE: DNA
```

<213> ORGANISM: artificial sequence
<220> FEATURE:
<223> OTHER INFORMATION: constructed chimeric gene

<400> SEQUENCE: 34

```
ccatggtgaa acgggggcg aagaagttgt ccatattggc cacgtttaaa tcaaaactgg      60
tgaaactcac ccagggattg gctgagacga aaaacatatt ctcaataaac cctttaggga    120
aataggccag gttttcaccg taacacgcca catcttgcga atatatgtgt agaaactgcc    180
ggaaatcgtc gtggtattca ctccagagcg atgaaaacgt ttcagtttgc tcatggaaaa    240
cggtgtaaca agggtgaaca ctatcccata tcaccagctc accgtctttc attgccatac    300
ggaattagcg gccgcgttcg atcaacaacc cgaatcctat cgtaatgatg ttttgcccga    360
tcagcctcaa tcgacaattt tacgcgtttc gatcgaagca gggacgacaa ttggctggga    420
acggtatact ggaataaatg gtcttcgtta tggtattgat gtttttggtg catcggcccc    480
ggcgaatgat ctatatgctc atttcggctt gaccgcagtc ggcatcacga caaggtgtt    540
ggccgcgatc gccggtaagt cggcacgtta aaaaatagct atggaatata atagctacta    600
ataagttagg agaataaaca tgcaagccta ttttgaccag ctcgatcgcg ttcgttatga    660
aggctcaaaa tcctcaaacc cgttagcatt ccgtcactac aatcccgacg aactggtgtt    720
gggtaagcgt atggaagagc acttgcgttt tgccgcctgc tactggcaca ccttctgctg    780
gaacggggcg gatatgtttg gtgtgggggc gtttaatcgt ccgtggcagc agcctggtga    840
ggcactggcg ttggcgaagc gtaaagcaga tgtcgcattt gagttttcc acaagttaca    900
tgtgccattt tattgcttcc acgatgtgga tgtttcccct gagggcgcgt cgttaaaaga    960
gtacatcaat aattttgcgc aaatggttga tgtcctggca ggcaagcaag aagagagcgg   1020
cgtgaagctg ctgtggggaa cggccaactg ctttacaaac cctcgctacg gcgcgggtgc   1080
ggcgacgaac ccagatcctg aagtcttcag ctgggcggca acgcaagttg ttacagcgat   1140
ggaagcaacc cataaattgg gcggtgaaaa ctatgtcctg tggggcggtc gtgaaggtta   1200
cgaaacgctg ttaaataccg acttgcgtca ggagcgtgaa caactgggcc gctttatgca   1260
gatggtggtt gagcataaac ataaaatcgg tttccagggc acgttgctta tcgaaccgaa   1320
accgcaagaa ccgaccaaac atcaatatga ttacgatgcc gcgacggtct atggcttcct   1380
gaaacagttt ggtctggaaa aagagattaa actgaacatt gaagctaacc acgcgacgct   1440
ggcaggtcac tctttccatc atgaaatagc caccgccatt gcgcttggcc tgttcggttc   1500
tgtcgacgcc aaccgtggcg atgcgcaact gggctgggac accgaccagt tcccgaacag   1560
tgtggaagag aatgcgctgg tgatgtatga aattctcaaa gcaggcggtt tcaccaccgg   1620
tggtctgaac ttcgatgcca agtacgtcg tcaaagtact gataaatatg atctgttta    1680
cggtcatatc ggcgcgatgg atacgatggc actggcgctg aaaattgcag cgcgcatgat   1740
tgaagatggc gagctggata acgcatcgc gcagcgttat tccggctgga atagcgaatt   1800
gggccagcaa atcctgaaag gccaaatgtc actggcagat ttagccaaat atgctcagga   1860
acatcatttg tctccggtgc atcagagtgg tcgccaggaa caactggaaa atctggtaaa   1920
ccattatctg ttcgacaaat aacggctaac tgtgcagtcc gttggcccgg ttatcggtag   1980
cgataccggg cattttttta aggaacgatc gat                                2013
```

<210> SEQ ID NO 35
<211> LENGTH: 40
<212> TYPE: DNA
<213> ORGANISM: artificial sequence
<220> FEATURE:

<223> OTHER INFORMATION: multi-cloning site oligo

<400> SEQUENCE: 35
aattctacct gcaggagtag gccggccatg agcgatcgca                                40

<210> SEQ ID NO 36
<211> LENGTH: 40
<212> TYPE: DNA
<213> ORGANISM: artificial sequence
<220> FEATURE:
<223> OTHER INFORMATION: multi-cloning site oligo

<400> SEQUENCE: 36
agcttgcgat cgctcatggc cggcctactc ctgcaggtag                                40

<210> SEQ ID NO 37
<211> LENGTH: 38
<212> TYPE: DNA
<213> ORGANISM: artificial sequence
<220> FEATURE:
<223> OTHER INFORMATION: primer

<400> SEQUENCE: 37
tcactcatgg ccggccgttc gatcaacaac ccgaatcc                                  38

<210> SEQ ID NO 38
<211> LENGTH: 39
<212> TYPE: DNA
<213> ORGANISM: artificial sequence
<220> FEATURE:
<223> OTHER INFORMATION: primer

<400> SEQUENCE: 38
ctactcatcc tgcaggccga tatacttatc gatcgttcc                                 39

<210> SEQ ID NO 39
<211> LENGTH: 40
<212> TYPE: DNA
<213> ORGANISM: artificial sequence
<220> FEATURE:
<223> OTHER INFORMATION: primer

<400> SEQUENCE: 39
catgccatgg gagctcgttc gatcaacaac ccgaatccta                                40

<210> SEQ ID NO 40
<211> LENGTH: 42
<212> TYPE: DNA
<213> ORGANISM: artificial sequence
<220> FEATURE:
<223> OTHER INFORMATION: primer

<400> SEQUENCE: 40
cacagcagag gtcacgttta ttctcctaac ttattaagta gc                             42

<210> SEQ ID NO 41
<211> LENGTH: 38
<212> TYPE: DNA
<213> ORGANISM: artificial sequence
<220> FEATURE:
<223> OTHER INFORMATION: primer

<400> SEQUENCE: 41
gttaggagaa taaacgtgac ctctgctgtg ccatcaaa                                  38

<210> SEQ ID NO 42

<211> LENGTH: 35
<212> TYPE: DNA
<213> ORGANISM: artificial sequence
<220> FEATURE:
<223> OTHER INFORMATION: primer

<400> SEQUENCE: 42
ccgctcgagc tagatattga actgaggatt cgaaa    35

<210> SEQ ID NO 43
<211> LENGTH: 903
<212> TYPE: DNA
<213> ORGANISM: artificial sequence
<220> FEATURE:
<223> OTHER INFORMATION: constructed chimeric gene

<400> SEQUENCE: 43
ccatggcgag ctcgttcgat caacaacccg aatcctatcg taatgatgtt ttgcccgatc    60
agcctcaatc gacaatttta cgcgtttcga tcgaagcagg gacgacaatt ggctgggaac   120
ggtatactgg aataaatggt cttcgttatg gtattgatgt ttttggtgca tcggccccgg   180
cgaatgatct atatgctcat ttcggcttga ccgcagtcgg catcacgaac aaggtgttgg   240
ccgcgatcgc cggtaagtcg gcacgttaaa aaatagctat ggaatataat agctacttaa   300
taagttagga gaataaacgt gacctctgct gtgccatcaa atacgaaaaa aaagctggtg   360
attgcttccg atcacgcagc atttgagttg aaatcaacct tgattacttg gctgaaagag   420
cttggtcatg aggtcgaaga ccttggcccct catgaaaaacc attcagtcga ttatcccgat   480
tacggttata agctggctgt cgctatcgca gaaaaaaccg ctgatttcgg tattgcttta   540
tgtggctcgg gaatcggtat ctcgatcgct gtcaatcgcc atccggctgc ccgttgcgct   600
ttgattacgg ataaccttac cgcccgtttg gcaagagaac ataacaatgc caatgttatc   660
gctatgggtg cgagattgat cggcattgaa accgctaagg attgtatttc agctttcctt   720
gcaacgccgt ttggaggtga acgtcatgtt cgccgtatcg ataaactttc gaatcctcag   780
ttcaatatct agctcgaggc ggcctgaacg tactgcaagt cctgacgtca ctgtgcagtc   840
cgttggcccg gttatcggta gcgataccgg gcatttttttt aaggaacgat cgatagcggc   900
cgc                                                                  903

<210> SEQ ID NO 44
<211> LENGTH: 22
<212> TYPE: DNA
<213> ORGANISM: artificial sequence
<220> FEATURE:
<223> OTHER INFORMATION: primer

<400> SEQUENCE: 44
atcaacaacc cgaatcctat cg    22

<210> SEQ ID NO 45
<211> LENGTH: 20
<212> TYPE: DNA
<213> ORGANISM: artificial sequence
<220> FEATURE:
<223> OTHER INFORMATION: primer

<400> SEQUENCE: 45
tatgctcaac caccatctgc    20

<210> SEQ ID NO 46
<211> LENGTH: 20
<212> TYPE: DNA

```
<213> ORGANISM: artificial sequence
<220> FEATURE:
<223> OTHER INFORMATION: primer

<400> SEQUENCE: 46
cgacatctgc tttacgcttc                                                   20

<210> SEQ ID NO 47
<211> LENGTH: 47
<212> TYPE: DNA
<213> ORGANISM: artificial sequence
<220> FEATURE:
<223> OTHER INFORMATION: portion of Zm Pgap with -190 position

<400> SEQUENCE: 47
aacggtatac tggaataaat ggtcttcgtt atggtattga tgttttt                     47

<210> SEQ ID NO 48
<211> LENGTH: 45
<212> TYPE: DNA
<213> ORGANISM: artificial sequence
<220> FEATURE:
<223> OTHER INFORMATION: portion of ZmPgap with -89 position

<400> SEQUENCE: 48
cggcatcacg aacaaggtgt tggccgcgat cgccggtaag tcggc                       45
```